United States Patent
Lee et al.

(10) Patent No.: US 11,765,921 B2
(45) Date of Patent: Sep. 19, 2023

(54) IONIC COMPOUND, AND COATING COMPOSITION AND ORGANIC LIGHT-EMITTING DEVICE COMPRISING SAME

(71) Applicant: LG Chem, Ltd., Seoul (KR)

(72) Inventors: Ho Gyu Lee, Daejeon (KR); Seog Jae Seo, Daejeon (KR); Jaesoon Bae, Daejeon (KR); Jaechol Lee, Daejeon (KR); Min Ho Hwang, Daejeon (KR); Jiyeon Shin, Daejeon (KR); Se Jin Jung, Daejeon (KR)

(73) Assignee: LG Chem, Ltd.

( * ) Notice: Subject to any disclaimer, the term of this patent is extended or adjusted under 35 U.S.C. 154(b) by 873 days.

(21) Appl. No.: 16/334,537

(22) PCT Filed: Nov. 24, 2017

(86) PCT No.: PCT/KR2017/013559
§ 371 (c)(1),
(2) Date: Mar. 19, 2019

(87) PCT Pub. No.: WO2018/097666
PCT Pub. Date: May 31, 2018

(65) Prior Publication Data
US 2020/0227645 A1    Jul. 16, 2020

(30) Foreign Application Priority Data
Nov. 25, 2016  (KR) .................. 10-2016-0158461

(51) Int. Cl.
*H10K 85/30* (2023.01)
*H10K 50/155* (2023.01)
(Continued)

(52) U.S. Cl.
CPC .......... *H10K 50/155* (2023.02); *C07C 25/02* (2013.01); *C07F 5/02* (2013.01); *C07F 5/027* (2013.01);
(Continued)

(58) Field of Classification Search
CPC .......... C07F 5/02; C08K 5/55; H01L 51/008; H10K 85/322
See application file for complete search history.

(56) References Cited

U.S. PATENT DOCUMENTS 5,427,991 A    6/1995   Turner
6,465,385 B1  10/2002  Sivak et al.
(Continued)

FOREIGN PATENT DOCUMENTS

CN    101185176 A    5/2008
CN    100486396 C    5/2009
(Continued)

OTHER PUBLICATIONS

Search Report from Office Action for Chinese Appiation No. 2017800630440 dated May 8, 2021; 4 pages.
(Continued)

*Primary Examiner* — Sean M DeGuire
(74) *Attorney, Agent, or Firm* — Lerner David LLP

(57) ABSTRACT

The present disclosure relates to an ionic compound, and a coating composition and an organic light emitting device including the same.

17 Claims, 2 Drawing Sheets

(51) Int. Cl.

| | | |
|---|---|---|
| *C08K 5/55* | (2006.01) | |
| *C08K 5/36* | (2006.01) | |
| *C08K 5/56* | (2006.01) | |
| *C07F 5/02* | (2006.01) | |
| *C09D 7/63* | (2018.01) | |
| *C07C 25/02* | (2006.01) | |
| *C09D 5/24* | (2006.01) | |
| *H10K 50/15* | (2023.01) | |
| *H10K 50/17* | (2023.01) | |
| *H10K 71/40* | (2023.01) | |
| *H10K 85/60* | (2023.01) | |
| *C08K 5/03* | (2006.01) | |
| *H10K 71/12* | (2023.01) | |
| *H10K 101/30* | (2023.01) | |

(52) U.S. Cl.
CPC ............... *C08K 5/36* (2013.01); *C08K 5/55* (2013.01); *C08K 5/56* (2013.01); *C09D 5/24* (2013.01); *C09D 7/63* (2018.01); *H10K 50/15* (2023.02); *H10K 50/17* (2023.02); *H10K 50/171* (2023.02); *H10K 71/40* (2023.02); *H10K 85/322* (2023.02); *H10K 85/60* (2023.02); *H10K 85/631* (2023.02); *H10K 85/636* (2023.02); *H10K 85/653* (2023.02); *H10K 85/655* (2023.02); *H10K 85/6572* (2023.02); *H10K 85/6576* (2023.02); *C08K 5/03* (2013.01); *H10K 71/12* (2023.02); *H10K 2101/30* (2023.02)

(56) References Cited

U.S. PATENT DOCUMENTS

| | | | |
|---|---|---|---|
| 10,101,658 B2 * | 10/2018 | Hirayama | G03F 7/322 |
| 11,228,011 B2 | 1/2022 | Lee et al. | |
| 2003/0152842 A1 * | 8/2003 | Cetin | G03F 7/0757 |
| | | | 430/1 |
| 2003/0198894 A1 * | 10/2003 | Mizutani | G03F 7/0045 |
| | | | 430/920 |
| 2007/0020479 A1 | 1/2007 | Uetani et al. | |
| 2007/0207341 A1 * | 9/2007 | Iida | H01L 51/006 |
| | | | 252/301.16 |
| 2009/0134779 A1 | 5/2009 | Kawami et al. | |
| 2010/0109000 A1 | 5/2010 | Mathai et al. | |
| 2010/0243992 A1 | 9/2010 | Tsuji et al. | |
| 2011/0089411 A1 | 4/2011 | Xia et al. | |
| 2011/0227047 A1 | 9/2011 | Wen et al. | |
| 2012/0001127 A1 | 1/2012 | Brown et al. | |
| 2012/0037894 A1 | 2/2012 | Okabe | |
| 2012/0074360 A1 | 3/2012 | Funyuu et al. | |
| 2014/0205951 A1 | 7/2014 | Ogihara et al. | |
| 2014/0291584 A1 | 10/2014 | Badre et al. | |
| 2014/0357896 A1 * | 12/2014 | Suzuki | C07C 381/12 |
| | | | 568/29 |
| 2015/0179963 A1 | 6/2015 | Bando et al. | |
| 2016/0020395 A1 | 1/2016 | Funyuu et al. | |
| 2016/0146987 A1 | 5/2016 | Ito et al. | |
| 2017/0299493 A1 | 10/2017 | Norton | |
| 2019/0019956 A1 * | 1/2019 | Gorohmaru | C07F 5/027 |
| 2019/0062351 A1 * | 2/2019 | Nakaie | C07F 5/027 |
| 2019/0280206 A1 | 9/2019 | Lee et al. | |

FOREIGN PATENT DOCUMENTS

| | | | |
|---|---|---|---|
| CN | 102077381 | A | 5/2011 |
| CN | 102449799 | A | 5/2012 |
| CN | 102959009 | A | 3/2013 |
| CN | 103865220 | A | 6/2014 |
| CN | 104365180 | A | 2/2015 |
| CN | 104604332 | A | 5/2015 |
| CN | 108884114 | A | 11/2018 |
| EP | 0710663 | A1 | 5/1996 |
| EP | 1725079 | A1 | 11/2006 |
| EP | 3434682 | A1 | 1/2019 |
| JP | H08127611 | A | 5/1996 |
| JP | H08143617 | A | 6/1996 |
| JP | H11286491 | A | 10/1999 |
| JP | 2000178281 | A | 6/2000 |
| JP | 2008063329 | A | 3/2008 |
| JP | 2009196982 | A | 9/2009 |
| JP | 2011525918 | A | 9/2011 |
| JP | 2012507151 | A | 3/2012 |
| JP | 4991648 | B2 | 8/2012 |
| JP | 2014122330 | A | 7/2014 |
| JP | 2014141585 | A | 8/2014 |
| JP | 2016060764 | A | 4/2016 |
| JP | 2019516959 | A | 6/2019 |
| JP | 2019520122 | A | 7/2019 |
| JP | 2019537835 | A | 12/2019 |
| JP | 2020500421 | A | 1/2020 |
| KR | 20110037972 | A | 4/2011 |
| KR | 20110134399 | A | 12/2011 |
| KR | 20140023246 | A | 2/2014 |
| KR | 20140063462 | A | 5/2014 |
| KR | 101422454 | B1 | 7/2014 |
| KR | 20150127077 | A | 11/2015 |
| KR | 20160041124 | A | 4/2016 |
| KR | 20160117284 | A | 10/2016 |
| WO | 2005089024 | A1 | 9/2005 |
| WO | 2009158069 | A1 | 12/2009 |
| WO | 2010104184 | A1 | 9/2010 |
| WO | 2014075298 | A1 | 5/2014 |
| WO | 2017164268 | A1 | 9/2017 |
| WO | 2017207327 | A1 | 12/2017 |

OTHER PUBLICATIONS

Search Report from Office Action for Chinese Application No. 201780072188.2 dated May 8, 2021; 4 pages.
Extended European Search Report including the Search Opinion for Application No. 17872963.8 dated Oct. 24, 2019, 8 pages.
Extended European Search Report including the Search Opinion for Application No. 17874454.6 dated Oct. 10, 2019, 8 pages.
Türp et al., "Synthesis of Nanometer-Sized, Rigid, and Hydrophobic Anions," Angewandte Chemie, International Ed., May 16, 2011, 123 (21), pp. 4962-4965.
International Search Report for PCT/KR2017/013549 dated Mar. 5, 2018.
International Search Report for PCT/KR2017/013554 dated Mar. 5, 2018.
International Search Report for PCT/KR2017/013558 dated Feb. 19, 2018.
International Search Report for PCT/KR2017/013559 dated Feb. 19, 2018.
Extended European Search Report including the Search Opinion for Application No. 17874046.0 dated Sep. 23, 2019, 8 pages.

* cited by examiner

[FIG. 1]
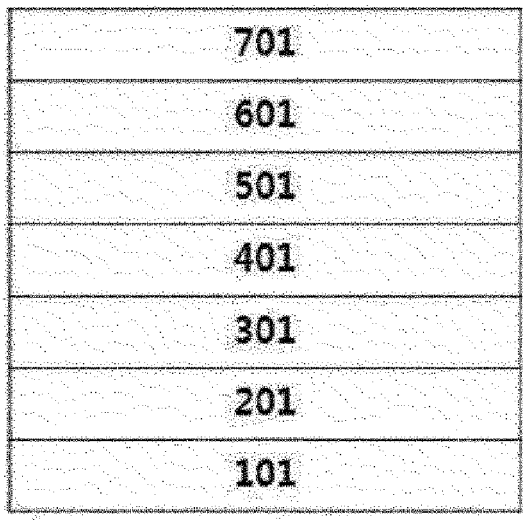
[FIG. 2]
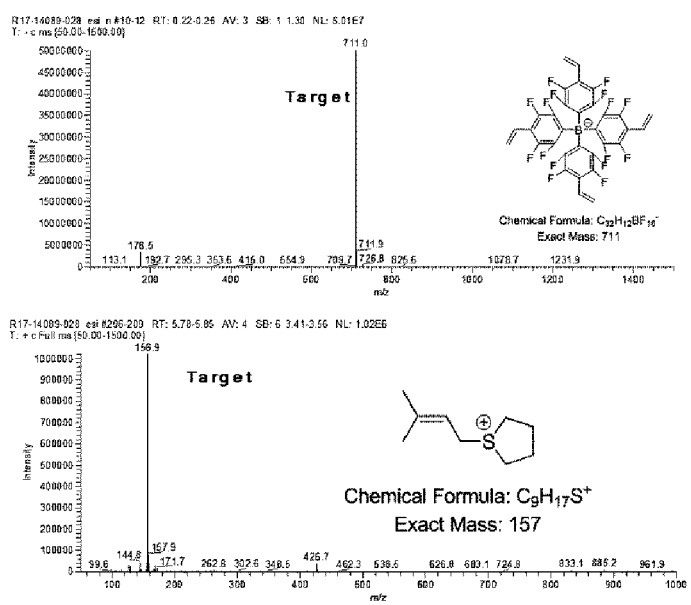

【FIG. 3】
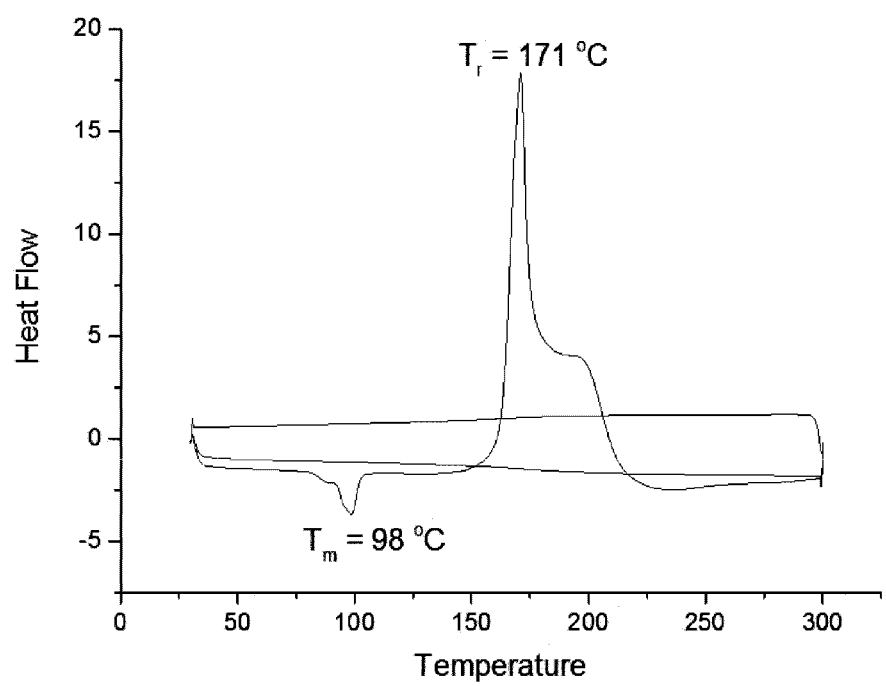

IONIC COMPOUND, AND COATING COMPOSITION AND ORGANIC LIGHT-EMITTING DEVICE COMPRISING SAME

CROSS-REFERENCE TO RELATED APPLICATIONS

The present application is a national phase entry under 35 U.S.C. § 371 of International Application No. PCT/KR2017/013559 filed Nov. 24, 2017, which claims priority from Korean Patent Application No. 10-2016-0158461 filed Nov. 25, 2016, all of which are incorporated herein by reference in their entirety.

TECHNICAL FIELD

The present specification relates to an ionic compound, and a coating composition and an organic light emitting device including the same.

BACKGROUND ART

An organic light emission phenomenon is one of examples converting a current to visible light by an internal process of specific organic molecules. A principle of an organic light emission phenomenon is as follows. When an organic material layer is placed between an anode and a cathode and a current is applied between the two electrodes, electrons and holes are injected to the organic material layer from the cathode and the anode, respectively. The holes and the electrons injected to the organic material layer recombine to form excitons, and light emits when these excitons fall back to the ground state. An organic light emitting device using such a principle may be generally formed with a cathode, an anode, and an organic material layer placed therebetween, for example, an organic material layer including a hole injection layer, a hole transfer layer, a light emitting layer and an electron transfer layer.

Materials used in an organic light emitting device are mostly pure organic materials or complex compounds in which organic materials and metals form complexes, and may be divided into hole injection materials, hole transfer materials, light emitting materials, electron transfer materials, electron injection materials and the like depending on the application. Herein, as the hole injection material or the hole transfer material, organic materials having a p-type property, that is, organic materials readily oxidized and having an electrochemically stable state when oxidized, are generally used. Meanwhile, as the electron injection material or the electron transfer material, organic materials having an n-type property, that is, organic materials readily reduced and having an electrochemically stable state when reduced, are generally used. As the light emitting layer material, materials having both a p-type property and an n-type property, that is, materials having a stable form in both oxidized and reduced states, are preferred, and materials having high light emission efficiency converting, when excitons are formed, the excitons to light are preferred.

In addition to the properties described above, it is preferred that materials used in an organic light emitting device additionally have properties as follows.

First, materials used in an organic light emitting device preferably have excellent thermal stability. This is due to joule heating produced by charge migration in the organic light emitting device. NPB normally used as a hole transfer layer material currently has a glass transition temperature of 100° C. or lower, and has a problem in that it is difficult to use in organic light emitting devices requiring a high current.

Second, in order to obtain a highly efficient organic light emitting device capable of low voltage driving, holes or electrons injected into the organic light emitting device need to be smoothly transferred to a light emitting layer, and at the same time, the injected holes and electrons need to be kept from escaping out of the light emitting layer. For this, materials used in the organic light emitting device need to have a proper band gap and a HOMO or LUMO energy level. PEDOT:PSS currently used as a hole transfer material in an organic light emitting device manufactured using a solution coating method has a lower LUMO energy level compared to a LUMO energy level of organic materials used as a light emitting layer material, and therefore, has a problem in manufacturing an organic light emitting device with high efficiency and long lifetime.

In addition thereto, materials used in an organic light emitting device need to have excellent chemical stability, charge mobility, and interface property with electrodes or adjacent layers. In other words, materials used in an organic light emitting device need to undergo less material deformation caused by moisture or oxygen. In addition, by having proper hole or electron mobility, the materials need to maximize exciton formation through balancing hole and electron density in a light emitting layer of the organic light emitting device. For device stability, the materials also need to improve an interface with electrodes including metals or metal oxides.

Accordingly, development of organic materials fulfilling such requirements has been required in the art.

DISCLOSURE

Technical Problem

The present specification is directed to providing an ionic compound, and a coating composition and an organic light emitting device including the same.

Technical Solution

One embodiment of the present specification provides an ionic compound including an anion group represented by the following Chemical Formula 1; and a cation group represented by the following Chemical Formula 2.

[Chemical Formula 1]

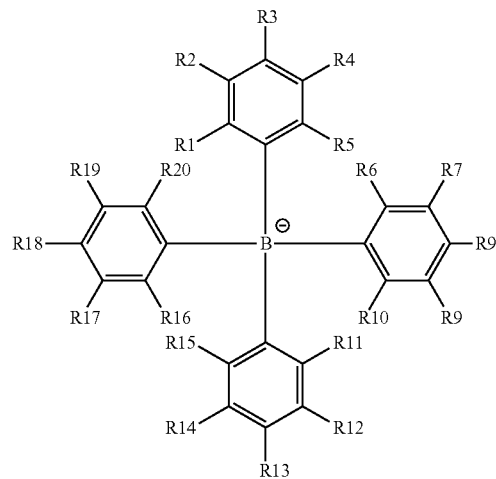

In Chemical Formula 1, at least one of R1 to R20 is F, a cyano group, or a substituted or unsubstituted fluoroalkyl group, at least one of the remaining R1 to R20 is a curing group, the remaining R1 to R20 are the same as or different from each other, and each independently hydrogen; deuterium; a nitro group; —C(O) $R_{100}$; —$OR_{101}$; —$SR_{102}$; —$SO_3R_{103}$; —$COOR_{104}$; —$OC(O)R_{105}$; —$C(O)NR_{106}R_{107}$; a substituted or unsubstituted alkyl group; a substituted or unsubstituted fluoroalkyl group; a substituted or unsubstituted alkenyl group; a substituted or unsubstituted alkynyl group; a substituted or unsubstituted amine group; a substituted or unsubstituted aryl group; or a substituted or unsubstituted heterocyclic group, and $R_{100}$ to $R_{107}$ are the same as or different from each other, and each independently hydrogen; deuterium; or a substituted or unsubstituted alkyl group.

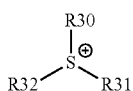

[Chemical Formula 2]

In Chemical Formula 2,

R30 to R32 are the same as or different from each other, and each independently a substituted or unsubstituted alkyl group; a substituted or unsubstituted alkenyl group; a substituted or unsubstituted alkynyl group; a substituted or unsubstituted cycloalkyl group; a substituted or unsubstituted aryl group; a substituted or unsubstituted aryl group; or a substituted or unsubstituted heterocyclic group, or groups adjacent to each other bond to each other to form a ring.

Another embodiment of the present specification provides a coating composition including the ionic compound described above.

Still another embodiment of the present specification provides an organic light emitting device including a first electrode; a second electrode; and one or more organic material layers provided between the first electrode and the second electrode, wherein one or more layers of the organic material layers include a cured material of the coating composition described above.

Advantageous Effects

A compound according to one embodiment of the present specification includes a functional group polymerized by heat or light, and when providing sufficient heat or light after forming a film, tolerance to a solvent for a process is developed, and properties of the film do not change since washing off of the compound according to one embodiment of the present specification or migration of interlayer materials is prevented, and as a result, an organic light emitting device having reproducibility can be manufactured.

The compound according to one embodiment of the present specification is an ionic monomer and dissolved in a solvent coated through a solution process, and then formed to a film through heat treatment or UV treatment, and particularly, the compound according to the present specification can provide a low driving voltage, high light emission efficiency and a high lifetime property when cured at around 200° C.

DESCRIPTION OF DRAWINGS

FIG. 1 illustrates an example of an organic light emitting device according to one embodiment of the present specification.

FIG. 2 is an MS spectrum of Compound 4 according to one embodiment of the present specification.

FIG. 3 is a DSC spectrum of Compound 4 according to one embodiment of the present specification.

REFERENCE NUMERAL

101: Substrate
201: Anode
301: Hole Injection Layer
401: Hole Transfer Layer
501: Light Emitting Layer
601: Electron Transfer Layer
701: Cathode

MODE FOR DISCLOSURE

Hereinafter, the present specification will be described in more detail.

In the present specification, a description of a certain member being placed "on" another member includes not only a case of the one member adjoining the another member but a case of still another member being present between the two members.

In the present specification, a description of a certain part "including" certain constituents means capable of further including other constituents, and does not exclude other constituents unless particularly stated on the contrary.

Throughout the specification of the present application, the term "combination thereof" included in a Markush-type expression means a mixture or a combination of one or more selected from the group consisting of constituents described in the Markush-type expression, and means including one or more selected from the group consisting of the constituents.

One embodiment of the present specification provides an ionic compound including an anion group represented by Chemical Formula 1; and a cation group represented by Chemical Formula 2.

In the present specification, a "curing group" may mean a reactive substituent crosslinking compounds by being exposed to heat and/or light. The crosslinking may be produced while linking radicals produced by decomposing carbon-carbon multiple bonds or cyclic structures through heat treatment or light irradiation.

In one embodiment of the present specification, the curing group is selected from a group of the following curing groups.

[Group of Curing Groups]

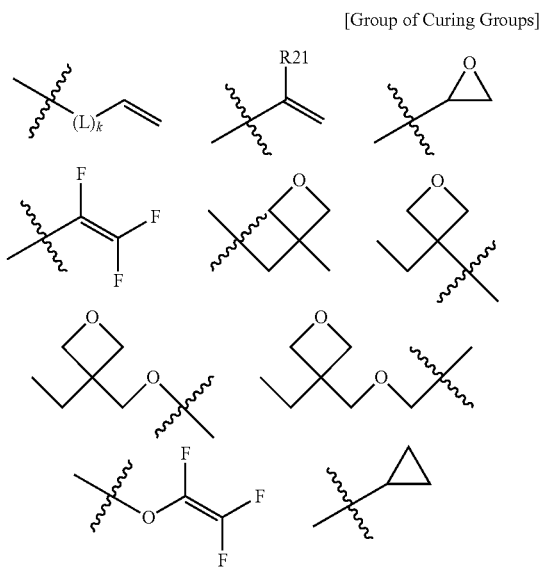

-continued

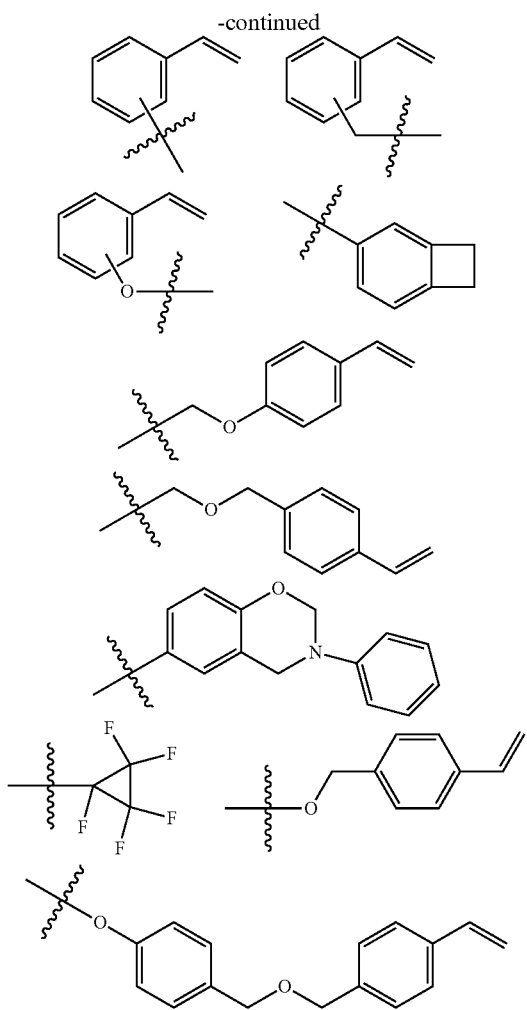

In the group of the curing groups, L is a direct bond; O; S; a substituted or unsubstituted alkylene group; a substituted or unsubstituted arylene group; or a substituted or unsubstituted divalent heterocyclic group, k is an integer of 1 or 2, and when k is 2, substituents in the parentheses are the same as or different from each other, and R21 is a substituted or unsubstituted alkyl group.

In one embodiment of the present specification, various curing groups may be used as the curing group as long as it is a curing group capable of curing, and the curing group is not limited to the group of the curing groups.

Hereinafter, substituents of the present specification will be described below in detail, however, the substituents are not limited thereto.

In the present specification,

means a site bonding to other substituents or bonding sites.

The term "substitution" in the present specification means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one or more substituents selected from the group consisting of hydrogen; deuterium; a halogen group; an alkyl group; a cycloalkyl group; an alkoxy group; an aryloxy group; an aryl group; an amine group; an arylamine group; and a curing group, or being unsubstituted, or being substituted with a substituent linking two or more substituents among the substituents illustrated above, or being unsubstituted.

In the present specification, examples of the halogen group may include fluorine, chlorine, bromine or iodine.

In the present specification, the alkyl group may be linear, branched or cyclic, and although not particularly limited thereto, the number of carbon atoms is preferably from 1 to 50. Specific examples thereof may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, the alkoxy group may be linear, branched or cyclic. The number of carbon atoms of the alkoxy group is not particularly limited, but is preferably from 1 to 30. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benxyloxy, p-methylbenzyloxy and the like, but are not limited thereto.

The alkyl group may be substituted with an aryl group or a heterocyclic group to function as an arylalkyl group or a heteroarylalkyl group. The aryl group and the heterocyclic group may be selected from among examples of an aryl group or a heterocyclic group to describe below.

In the present specification, the length of the alkyl group does not affect a conjugation length of the compound, and may affect the use of the compound in an organic light emitting device, for example, the use of a vacuum deposition method or a solution coating method.

In the present specification, the cycloalkyl group is not particularly limited, but preferably has 3 to 60 carbon atoms, and specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

When the aryl group is a monocyclic aryl group in the present specification, the number of carbon atoms is not particularly limited, but is preferably from 6 to 25. Specific examples of the monocyclic aryl group may include a phenyl group, a biphenyl group, a terphenyl group, a quaterphenyl group and the like, but are not limited thereto.

When the aryl group is a multicyclic aryl group, the number of carbon atoms is not particularly limited, but is preferably from 10 to 30. Specific examples of the multicyclic aryl group may include a naphthyl group, an anthracenyl group, a phenanthryl group, a pyrenyl group, a perylenyl group, a chrysenyl group, a fluorenyl group and the like, but are not limited thereto.

In the present specification, the fluorenyl group may be substituted, and adjacent substituents may bond to each other to form a ring.

When the fluorenyl group is substituted,

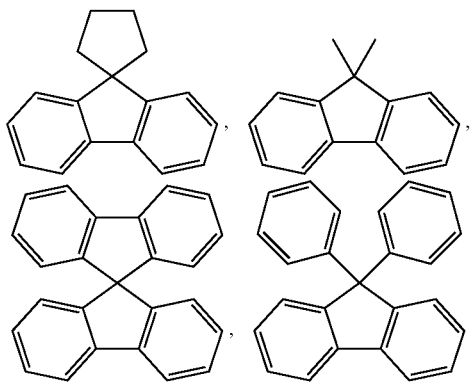

and the like may be included. However, the structure is not limited thereto.

The aryl group may be substituted with an alkyl group or an alkoxy group to function as an arylalkyl group or an aryloxy group. The alkyl group or the alkoxy group may be selected from among the examples described above.

In the present specification, the number of carbon atoms of the amine group is not particularly limited, but is preferably from 1 to 30. The amine group may be substituted with the above-described alkyl group, aryl group, heterocyclic group, alkenyl group, cycloalkyl group, combinations thereof, and the like, and specific examples of the amine group may include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group and the like, but are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a multicyclic aryl group. The arylamine group including two or more aryl groups may include monocyclic aryl groups, multicyclic aryl groups, or both monocyclic aryl groups and multicyclic aryl groups. For example, the aryl group in the arylamine group may be selected from among the examples of the aryl group described above. Specific examples of the arylamine group may include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenylamine group and the like, but are not limited thereto.

In the present specification, the heterocyclic group includes one or more atoms that are not carbon, that is, heteroatoms, and specifically, the heteroatom may include one or more atoms selected from the group consisting of O, N, Se, S and the like. The number of carbon atoms is not particularly limited, but is preferably from 2 to 30, and the heteroaryl group may be monocyclic or multicyclic. Examples of the heterocyclic group may include a thiophene group, a furanyl group, a pyrrole group, an imidazolyl group, a triazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group, an isoxazolyl group, a thiadiazolyl group, a phenothiazinyl group, a dibenzofuranyl group and the like, but are not limited thereto.

In the present specification, the arylene group means the aryl group having two bonding sites, that is, a divalent group. Descriptions on the aryl group provided above may be applied thereto except for each being a divalent.

In the present specification, the divalent heterocyclic group means the heterocyclic group having two bonding sites, that is, a divalent group. Descriptions on the heterocyclic group provided above may be applied thereto except for each being a divalent.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the ring formed by adjacent groups bonding to each other may be monocyclic or multicyclic, may be aliphatic, aromatic, or a fused ring of aliphatic or aromatic, and may form a hydrocarbon ring or a heteroring.

In one embodiment of the present specification, the number of the curing group of the anion group represented by Chemical Formula 1 is 1.

In one embodiment of the present specification, the number of the curing group of the anion group represented by Chemical Formula 1 is 2.

In one embodiment of the present specification, the number of the curing group of the anion group represented by Chemical Formula 1 is 4. When the anion group represented by Chemical Formula 1 does not have a curing group, curing does not occur, and device properties may decline due to migration of a cation group and an anion group of the present specification between electrode layers. In addition, as the number of the curing group increases, a coating composition curing rate increases and a film retention rate is enhanced, and therefore, compounds having 4 curing groups are more preferred.

In one embodiment of the present specification, the number of the F, the cyano group, or the substituted or unsubstituted fluoroalkyl group in the anion group represented by Chemical Formula 1 is from 16 to 19.

In one embodiment of the present specification, parts by weight of the F in the anion group is from 15 parts by weight to 50 parts by weight or less with respect to 100 parts by weight of the anion group.

In one embodiment of the present specification, parts by weight of the F in the anion group is from 10 parts by weight to 45 parts by weight or less.

In one embodiment of the present specification, the number of the F in the anion group is from 8 to 20.

In one embodiment of the present specification, the ionic compound including the anion group may be used in a hole injection layer of an organic light emitting device, and, when used in the hole injection layer, may be used as a dopant. Herein, when the F content of the anion group increases, an electron attracting force from other compounds (host compound) increases, and holes are more favorably formed in the host resulting in performance enhancement in the hole injection layer.

In one embodiment of the present specification, the F content may be analyzed using a COSA AQF-100 combustion furnace coupled to a Dionex ICS 2000 ion-chromatograph, or may be identified through 19F NMR, a method generally used for F analysis.

In one embodiment of the present specification, at least one benzene ring among the R1 to R5-bonding benzene ring, the R6 to R10-bonding benzene ring, the R11 to R15-bonding benzene ring, and the R16 to R20-bonding benzene ring in Chemical Formula 1 is selected from among the following structural formulae.

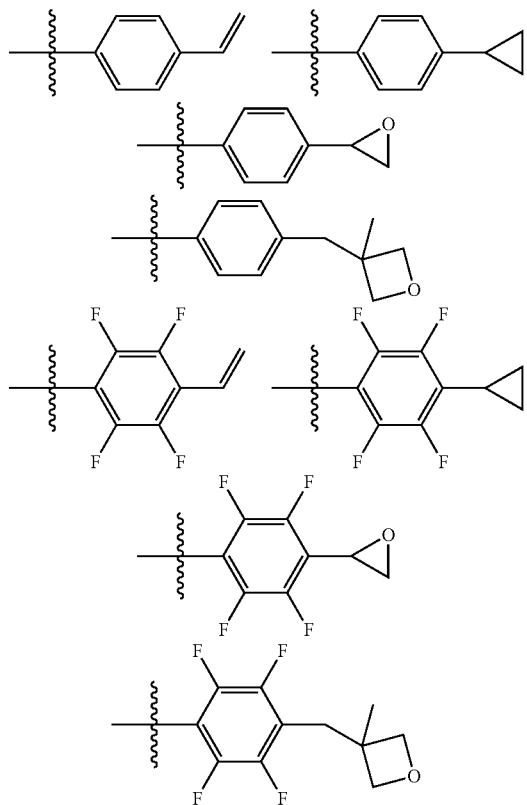

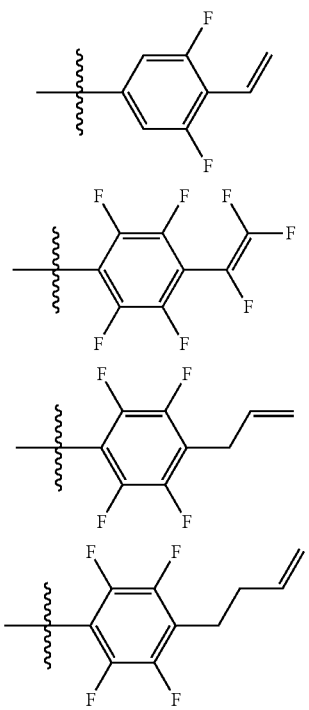

In one embodiment of the present specification, at least one benzene ring among the R1 to R5-bonding benzene ring, the R6 to R10-bonding benzene ring, the R11 to R15-bonding benzene ring, and the R16 to R20-bonding benzene ring in Chemical Formula 1 is selected from among the following structural formulae.

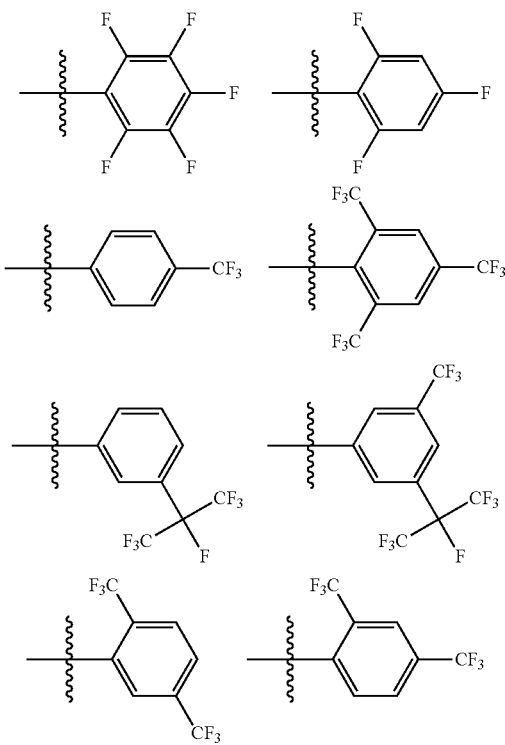

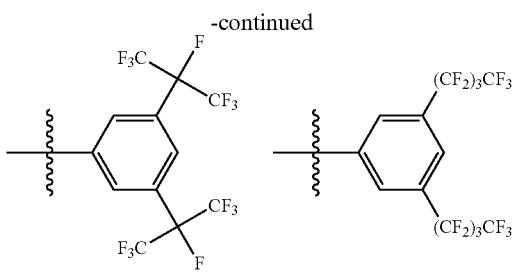

In one embodiment of the present specification, the anion group represented by Chemical Formula 1 is represented by the following Chemical Formula 1-1.

[Chemical Formula 1-1]

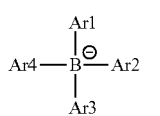

In Chemical Formula 1-1,

Ar1 to Ar4 are the same as or different from each other, at least one of Ar1 to Ar4 is represented by the following Chemical Formula 1-2, and the remaining Ar1 to Ar4 are represented by the following Chemical Formula 1-3,

[Chemical Formula 1-2]

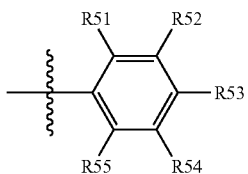

in Chemical Formula 1-2, at least one of R51 to R55 is F, a cyano group, or a substituted or unsubstituted fluoroalkyl group, at least one of the remaining R51 to R55 is a curing group, the remaining R51 to R55 are the same as or different from each other, and each independently hydrogen; deuterium; a nitro group; —C(O)R$_{100}$; —OR$_{101}$; —SR$_{102}$; —SO$_3$R$_{103}$; —COOR$_{104}$; —OC(O)R$_{105}$; —C(O)NR$_{106}$R$_{107}$; a substituted or unsubstituted alkyl group; a substituted or unsubstituted alkenyl group; a substituted or unsubstituted alkynyl group; a substituted or unsubstituted amine group; a substituted or unsubstituted aryl group; or a substituted or unsubstituted heterocyclic group, R$_{100}$ to R$_{107}$ are the same as or different from each other, and each independently hydrogen; deuterium; or a substituted or unsubstituted alkyl group,

[Chemical Formula 1-3]

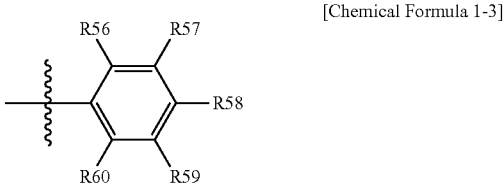

in Chemical Formula 1-3, at least one of R56 to R60 is a curing group, the remaining R56 to R60 are the same as or different from each other, and each independently hydrogen; deuterium; a nitro group; —C(O) R$_{100}$; —OR$_{101}$; —SR$_{102}$; —SO$_3$R$_{103}$; —COOR$_{104}$; —OC(O)R$_{105}$; —C(O)NR$_{106}$R$_{107}$; a substituted or unsubstituted alkyl group; a substituted or unsubstituted fluoroalkyl group; a substituted or unsubstituted alkenyl group; a substituted or unsubstituted alkynyl group; a substituted or unsubstituted amine group; a substituted or unsubstituted aryl group; or a substituted or unsubstituted heterocyclic group, and R$_{100}$ to R$_{107}$ are the same as described above.

In one embodiment of the present specification, the anion group is any one selected from among the following structural formulae.

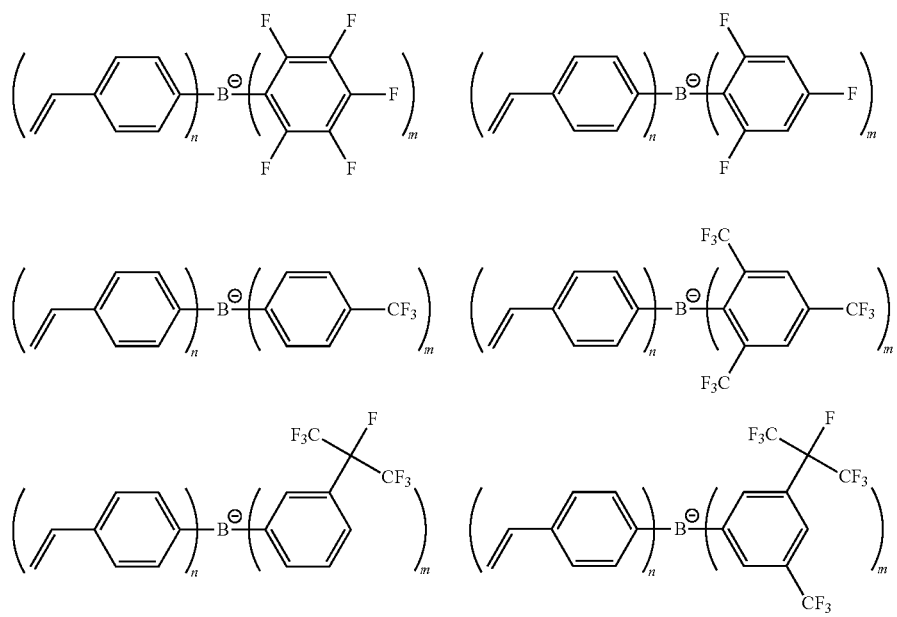

-continued
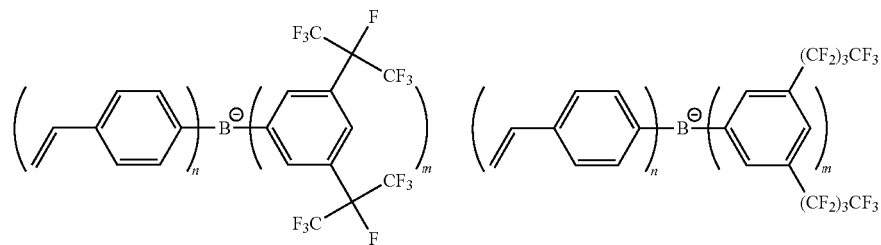
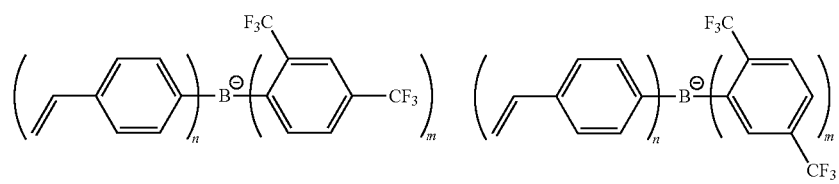
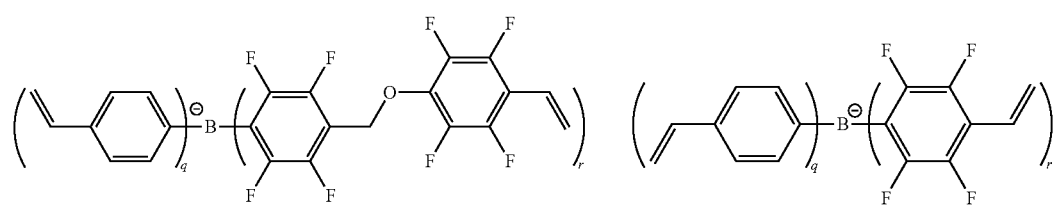
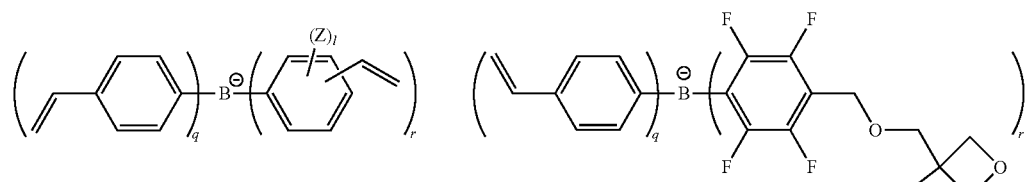
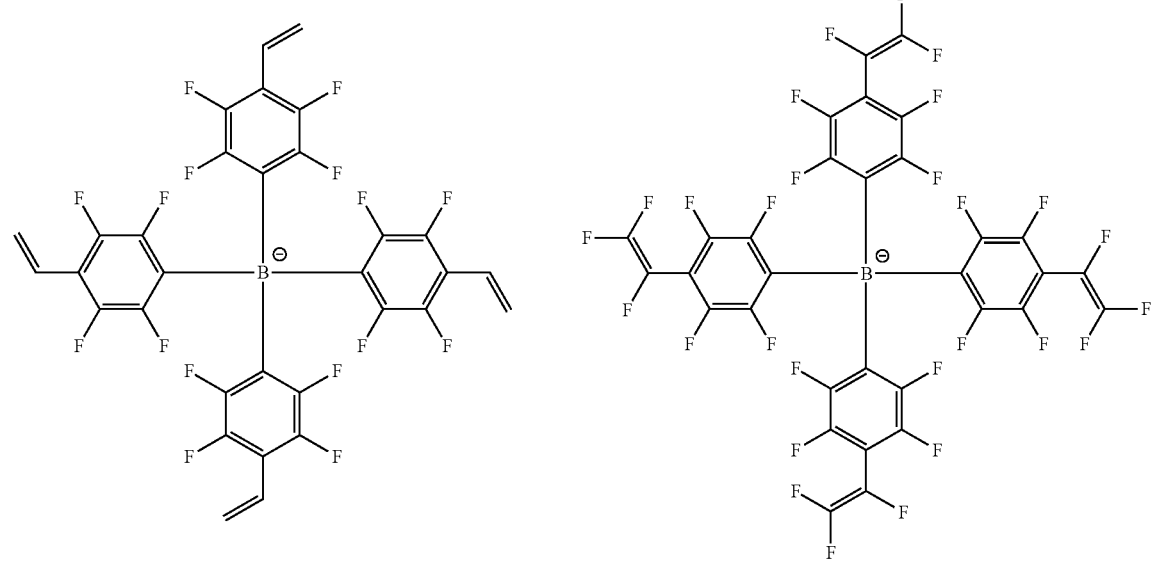

-continued
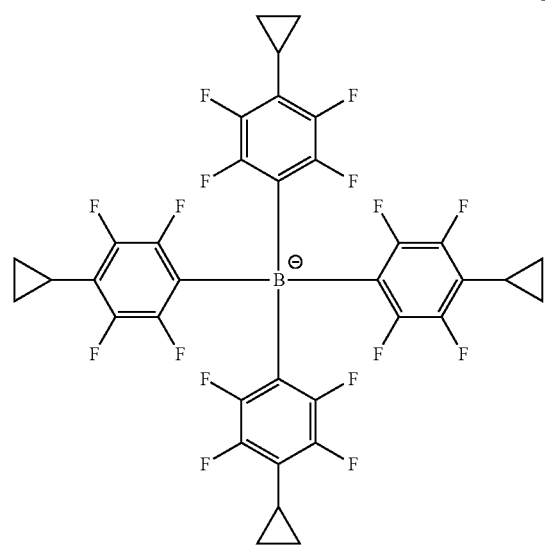
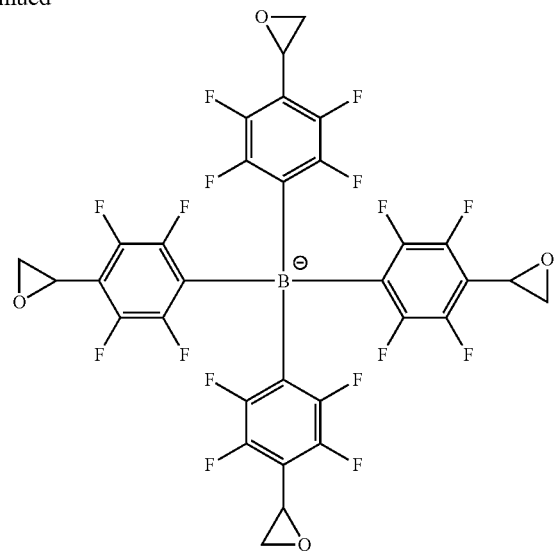
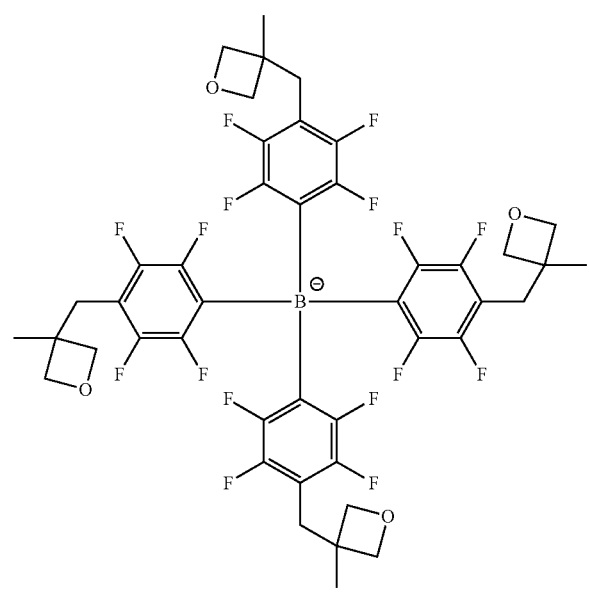
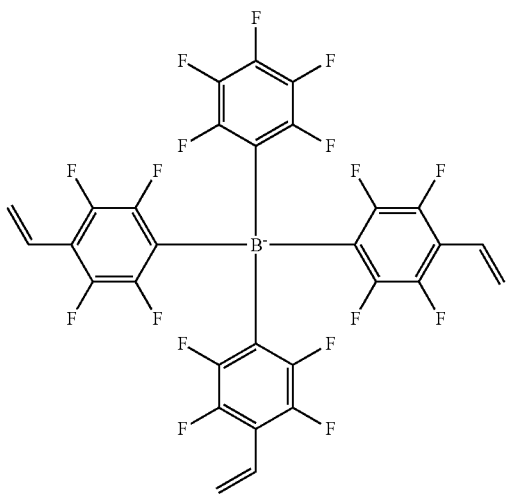
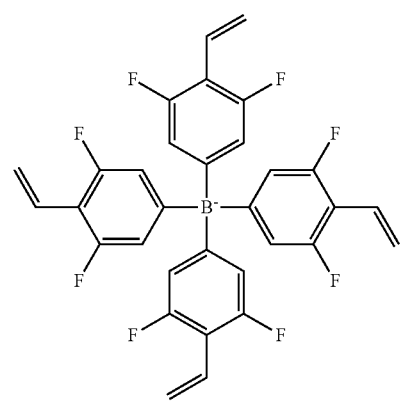

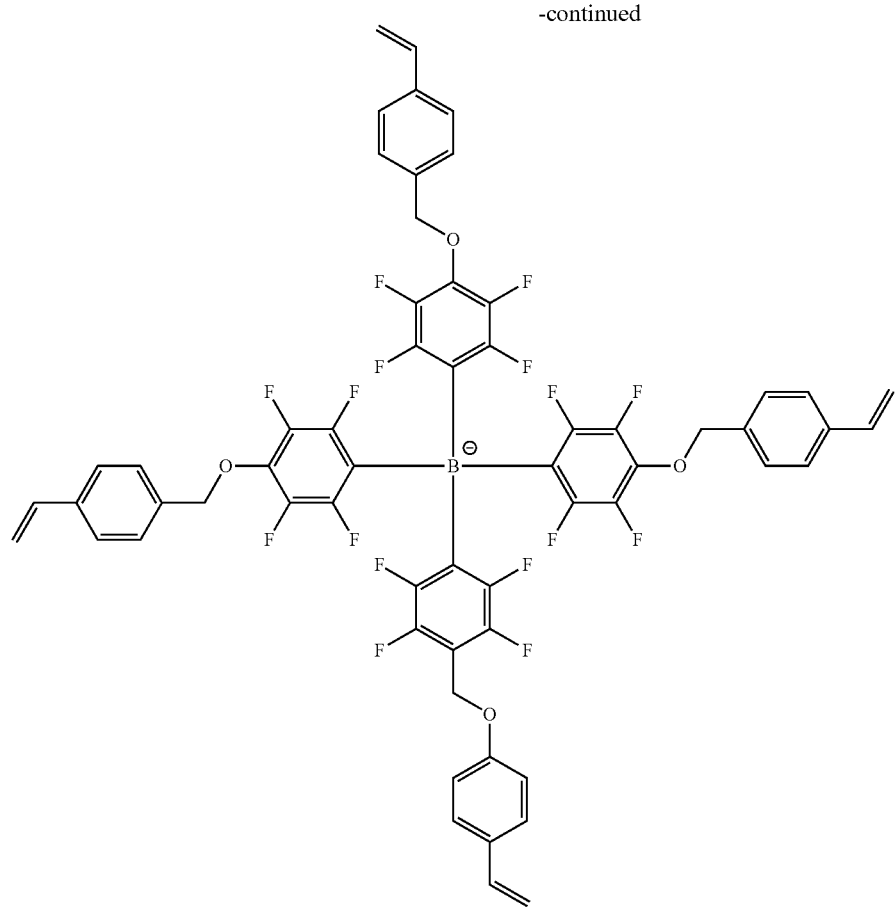
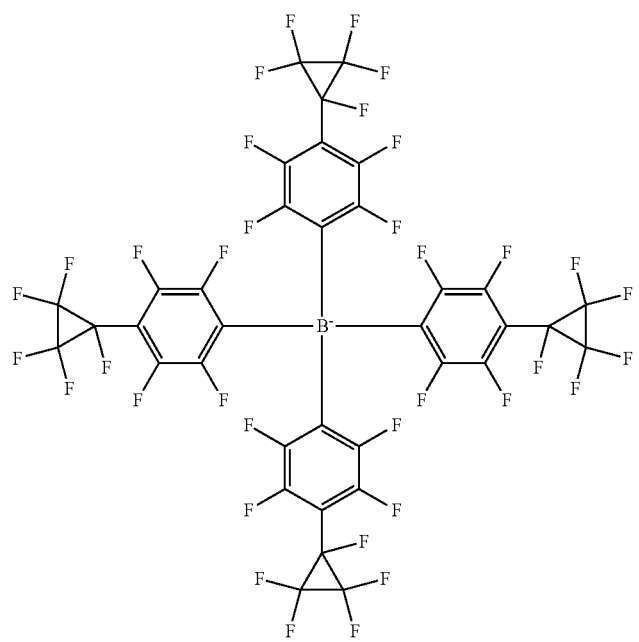

-continued

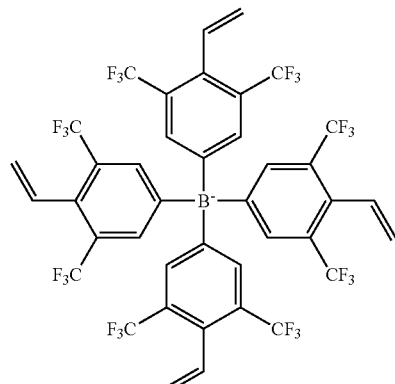
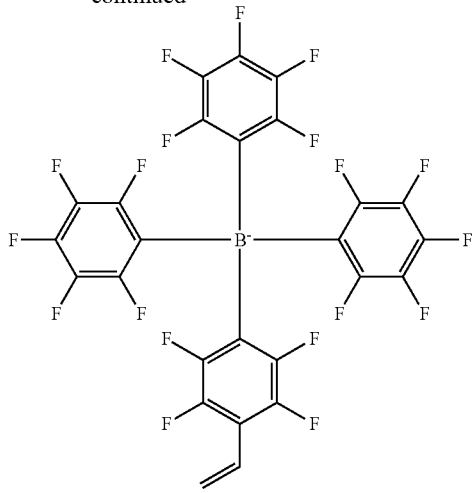

In the structural formulae, n is an integer of 1 to 3, m is an integer of 1 to 3, and m+n=4, q is an integer of 0 to 3, r is an integer of 1 to 4, and q+r=4, Z is deuterium; a halogen group; a nitro group; a cyano group; an amino group; —C(O)$R_{100}$; —O$R_{101}$; —S$R_{102}$; —S$O_3R_{103}$; —COO$R_{104}$; —OC(O)$R_{105}$; —C(O)N$R_{106}R_{107}$; a substituted or unsubstituted alkyl group; a substituted or unsubstituted alkenyl group; a substituted or unsubstituted alkynyl group; a substituted or unsubstituted amine group; a substituted or unsubstituted aryl group; or a substituted or unsubstituted heterocyclic group, l is an integer of 1 to 4, and when 1 is 2 or greater, Zs are the same as or different from each other, and $R_{100}$ to $R_{107}$ are the same as or different from each other, and each independently hydrogen; deuterium; or a substituted or unsubstituted alkyl group.

In the present specification, the cation group of Chemical Formula 2 is a compound produced by coordinate bonding hydrogen ions or other organic radicals to a sulfur electron pair.

In one embodiment of the present specification, the cation group of Chemical Formula 2 is represented by any one of the following Chemical Formulae 2-1 to 2-4.

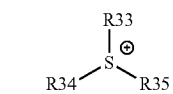

[Chemical Formula 2-1]

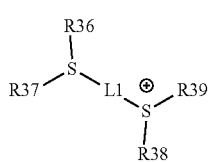

[Chemical Formula 2-2]

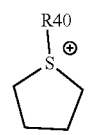

[Chemical Formula 2-3]

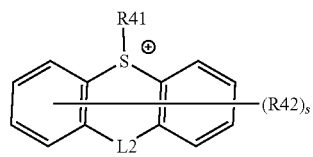

[Chemical Formula 2-4]

In Chemical Formulae 2-1 to 2-4,

R33 to R41 are the same as or different from each other, and each independently a substituted or unsubstituted alkyl group; a substituted or unsubstituted alkenyl group; a substituted or unsubstituted cycloalkyl group; or a substituted or unsubstituted aryl group, L1 is a substituted or unsubstituted arylene group, L2 is a direct bond; O; S; or C=O, and R42 is a substituted or unsubstituted carbonyl group, and s is 0 or 1.

In one embodiment of the present specification, the compounds of Chemical Formulae 2-1 and 2-2 are a linear or branched compound compared to other sulfonium cation groups, and therefore, has high solubility compared to cyclic compounds, which leads to an effect of favorable solution processability.

In one embodiment of the present specification, the compounds of Chemical Formulae 2-3 and 2-4 have high stability compared to other sulfonium cation groups, which leads to an effect of superior device performance.

In one embodiment of the present specification, R30 to R32 are the same as or different from each other, and each independently a substituted or unsubstituted phenyl group; a substituted or unsubstituted cyclopropyl group; a substituted or unsubstituted ethyl group; a substituted or unsubstituted methyl group; or a substituted or unsubstituted fluorenyl group.

In one embodiment of the present specification, R30 to R32 are the same as or different from each other, and each independently a phenyl group unsubstituted or substituted with one or more substituents selected from the group consisting of a methyl group, a vinyl group, butenyl, an ester group, a phenyl group, a butyl group, an ethyl group, a methoxy group and a hydroxyl group; a cyclopropyl group unsubstituted or substituted with one or more substituents selected from the group consisting of a methyl group, a vinyl group, butenyl, an ester group, a phenyl group, a butyl group, an ethyl group, a methoxy group and a hydroxyl group; an ethyl group unsubstituted or substituted with one or more substituents selected from the group consisting of a methyl group, a vinyl group, butenyl, an ester group, a phenyl group, a butyl group, an ethyl group, a methoxy group and a hydroxyl group; a methyl group unsubstituted or substituted with one or more substituents selected from the group consisting of a methyl group, a vinyl group, butenyl, an ester group, a phenyl group, a butyl group, an ethyl group, a methoxy group and a hydroxyl group; or a fluorenyl group unsubstituted or substituted with one or more substituents selected from the group consisting of a methyl group, a vinyl group, butenyl, an ester group, a phenyl group, a butyl group, an ethyl group, a methoxy group and a hydroxyl group.

In one embodiment of the present specification, the cation group represented by Chemical Formula 2 is selected from among the following structural formulae.

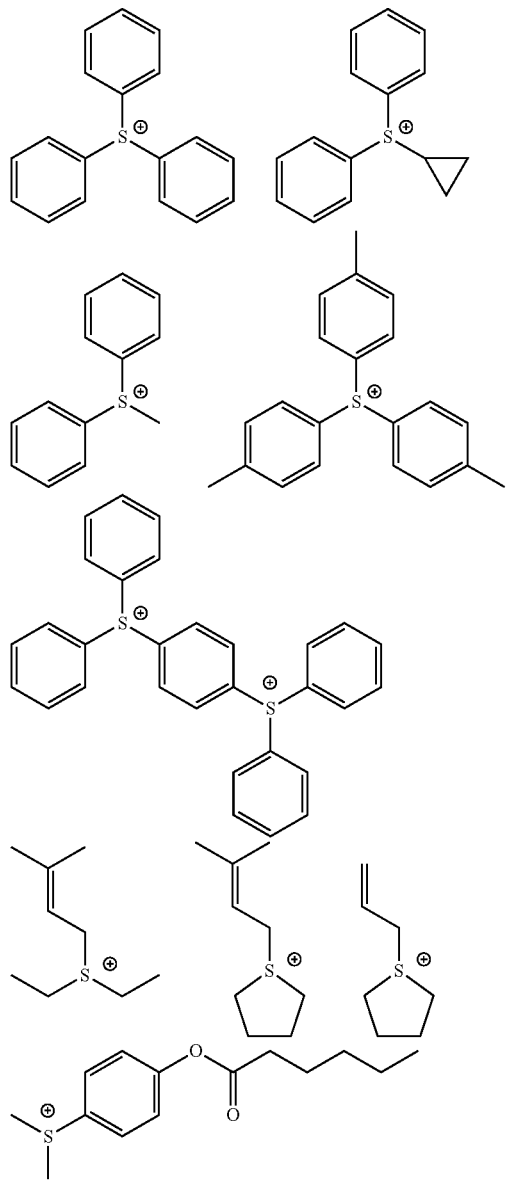

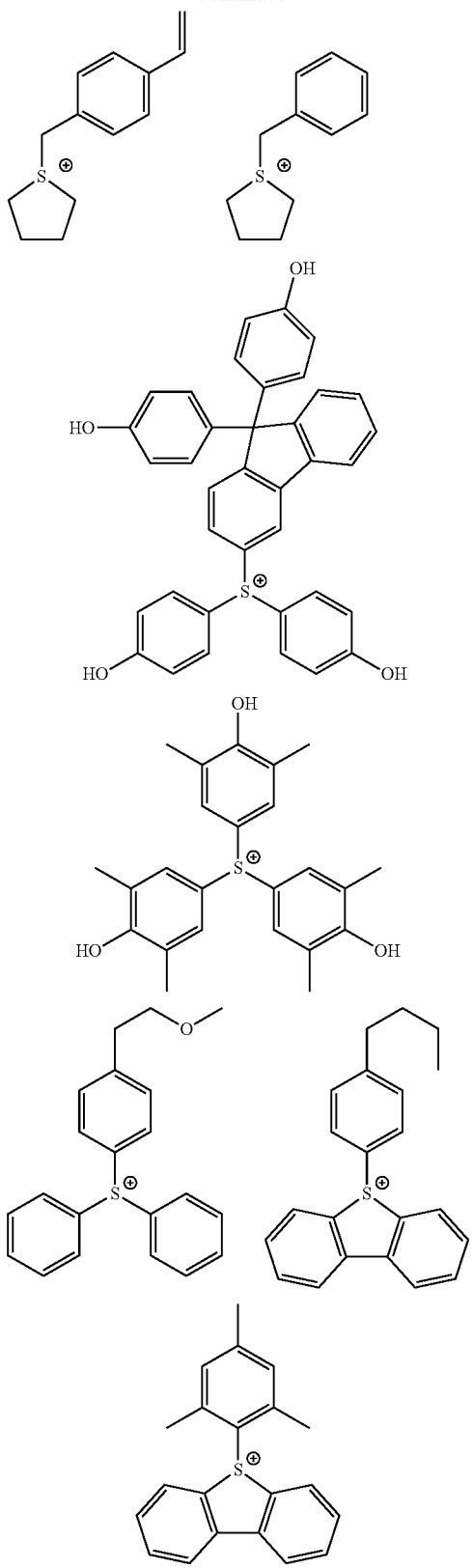

In one embodiment of the present specification, the ionic compound is selected from among the following structural formulae.

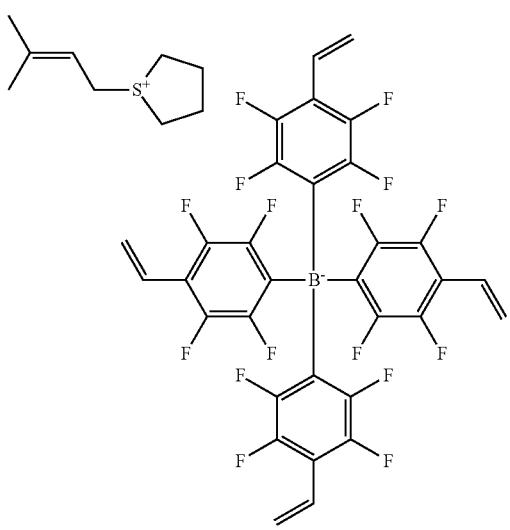

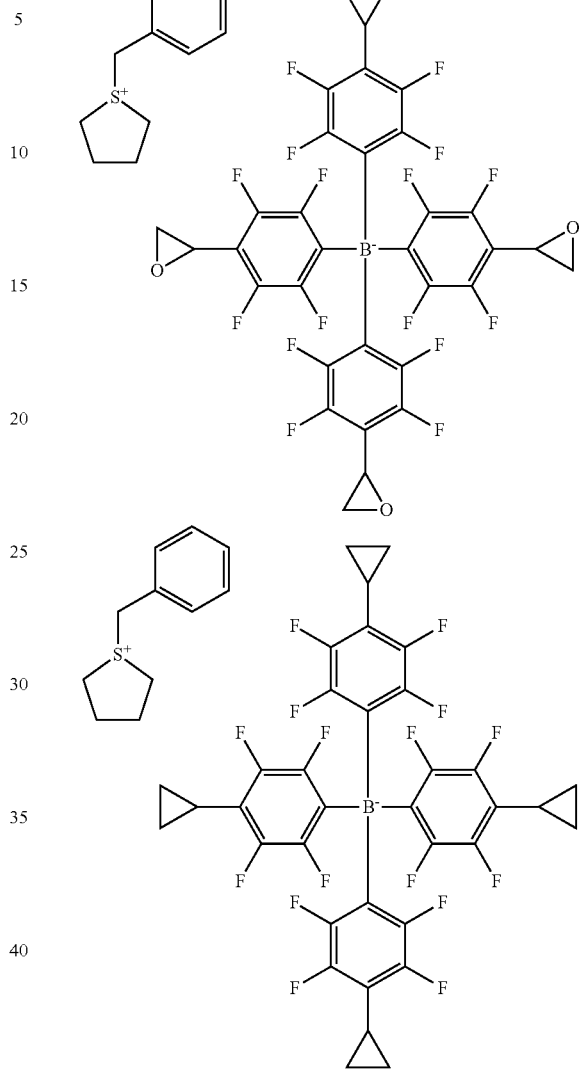

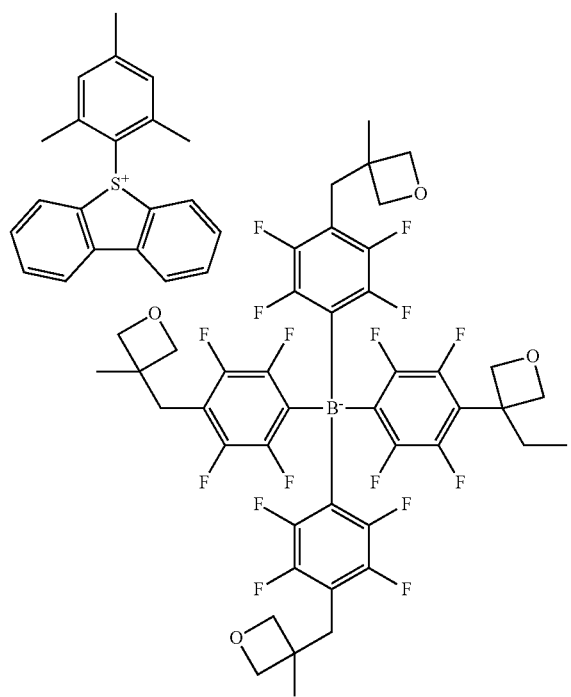

In one embodiment of the present specification, a coating composition including the ionic compound including the anion group of Chemical Formula 1 and the cation group of Chemical Formula 2 is provided.

In one embodiment of the present specification, the anion group represented by Chemical Formula 1 and the cation group represented by Chemical Formula 2 are included in an equivalent ratio of 1:5 to 5:1.

In one embodiment of the present specification, the anion group represented by Chemical Formula 1 and the cation group represented by Chemical Formula 2 are included in an equivalent ratio of 1:1.

In one embodiment of the present specification, the coating composition is for coating an organic material layer of an organic light emitting device.

In one embodiment of the present specification, the ionic compound including the anion group represented by Chemical Formula 1 preferably includes compounds having solubility for proper organic solvents. In one embodiment of the present specification, the coating composition may be a liquid phase. The "liquid phase" means in a liquid state at room temperature and atmospheric pressure.

In one embodiment of the present specification, examples of the solvent may include chlorine-based solvents such as chloroform, methylene chloride, 1,2-dichloroethane, 1,1,2-trichloroethane, chlorobenzene or o-dichlorobenzene; ether-based solvents such as tetrahydrofuran or dioxane; aromatic hydrocarbon-based solvents such as toluene, xylene, trimethylbenzene or mesitylene; aliphatic hydrocarbon-based solvents such as cyclohexane, methylcyclohexane, n-pentane, n-hexane, n-heptane, n-octane, n-nonane or n-decane; ketone-based solvents such as acetone, methyl ethyl ketone or cyclohexanone; ester-based solvents such as ethyl acetate, butyl acetate or ethyl cellosolve acetate; polyalcohols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin or 1,2-hexanediol, and derivatives thereof; alcohol-based solvents such as methanol, ethanol, propanol, isopropanol or cyclohexanol; sulfoxide-based solvents such as dimethyl sulfoxide; amide-based solvents such as N-methyl-2-pyrrolidone or N,N-dimethylformamide; benzoate-based solvents such as methyl benzoate, butyl benzoate or 3-phenoxybenzoate; tetraline, and the like, however, the solvent is not limited as long as it is a solvent capable of dissolving or dispersing the compound according to one embodiment of the present disclosure.

In another embodiment, the solvent may be used either alone as one type, or as a mixture mixing two or more solvent types.

In another embodiment, the solvent preferably has a boiling point of 40° C. to 250° C., and more preferably 60° C. to 230° C., however, the boiling point is not limited thereto.

In another embodiment, the single or mixed solvent preferably has viscosity of 1 CP to 10 CP, and more preferably 3 CP to 8 CP, however, the viscosity is not limited thereto.

In another embodiment, the coating composition preferably has a concentration of 0.1 wt/v % to 20 wt/v %, and more preferably 0.5 wt/v % to 5 wt/v %, however, the concentration is not limited thereto.

In one embodiment of the present specification, the coating composition may further include one, two or more types of additives selected from the group consisting of thermal polymerization initiators and photopolymerization initiators.

Examples of the thermal polymerization initiator may include peroxides such as methyl ethyl ketone peroxide, methyl isobutyl ketone peroxide, acetylacetone peroxide, methylcyclohexanone peroxide, cyclohexanone peroxide, isobutyryl peroxide, 2,4-dichlorobenzoyl peroxide, bis-3,5, 5-trimethyl hexanoyl peroxide, lauryl peroxide, benzoyl peroxide, p-chlorobenzoyl peroxide, dicumyl peroxide, 2,5-dimethyl-2,5-(t-butyloxy)-hexane, 1,3-bis(t-butylperoxyisopropyl)benzene, t-butyl cumyl peroxide, di-t-butyl peroxide, 2,5-dimethyl-2,5-(di-t-butylperoxy)hexane-3, tris-(t-butylperoxy)triazine, 1,1-di-t-butylperoxy-3,3,5-trimethylcyclohexane, 1,1-di-t-butylperoxycyclohexane, 2,2-di(t-butylperoxy)butane, 4,4-di-t-butylperoxy valeric acid n-butyl ester, 2,2-bis(4,4-t-butylperoxycyclohexyl)propane, t-butyl peroxyisobutyrate, di-t-butyl peroxyhexahydroterephthalate, t-butylperoxy-3,5,5-trimethylhexane, t-butyl peroxybenzoate or di-t-butyl peroxytrimethyl adipate; or azo-based such as azobis isobutylnitrile, azobis dimethylvaleronitrile or azobis cyclohexyl nitrile, but are not limited thereto.

Examples of the photopolymerization initiator may include acetophenone-based or ketal-based photopolymerization initiators such as diethoxyacetophenone, 2,2-dimethoxy-1,2-diphenyl ethan-1-one, 1-hydroxy-cyclohexyl-phenyl-ketone, 4-(2-hydroxyethoxy)phenyl-(2-hydroxy-2-propyl)ketone, 2-benzyl-2-dimethylamino-1-(4-morpholinophenyl)butanone-1,2-hydroxy-2-methyl-1-phenylpropan-1-one, 2-methyl-2-morpholino(4-methylthiophenyl)propan-1-one or 1-phenyl-1,2-propanedion-2-(o-ethoxycarbonyl)oxime; benzoin ether-based photopolymerization initiators such as benzoin, benzoin methyl ether, benzoin ethyl ether, benzoin isobutyl ether or benzoin isopropyl ether; benzophenone-based photopolymerization initiators such as benzophenone, 4-hydroxybenzophenone, 2-benzoylnaphthalene, 4-benzoylbiphenyl, 4-benzoyl phenyl ether, acrylated benzophenone or 1,4-benzoylbenzene; thioxanthone-based photopolymerization initiators such as 2-isopropylthioxanthone, 2-chlorothioxanthone, 2,4-dimethylthioxanthone, 2,4-diethylthioxanthone or 2,4-dichlorothioxanthone; and, as other photopolymerization initiators, ethyl anthraquinone, 2,4,6-trimethylbenzoyldiphenylphosphine oxide, 2,4,6-trimethylbenzoylphenylethoxyphosphine oxide, bis(2,4,6-trimethylbenzoyl)phenylphosphine oxide, bis(2,4-dimethoxybenzoyl)-2,4,4-trimethylpentylphosphine oxide, methylphenylglyoxyester, 9,10-phenanthrene, acridine-based compounds, triazine-based compounds, imidazole-based compounds, and the like. In addition, those having a photopolymerization facilitating effect may be used either alone or together with the photopolymerization initiator. Examples thereof may include triethanolamine, methyldiethanolamine, ethyl 4-dimethylaminobenzoate, isoamyl 4-dimethylaminobenzoate, (2-dimethylamino)ethyl benzoate, 4,4'-dimethylaminobenzophenone and the like, but are not limited thereto.

Another embodiment of the present specification provides an organic light emitting device formed using the coating composition.

In one embodiment of the present specification, the organic light emitting device includes a first electrode; a second electrode; and one or more organic material layers provided between the first electrode and the second electrode, wherein one or more layers of the organic material layers are formed using a coating composition including the ionic compound including the anion group of Chemical Formula 1; and the cation group of Chemical Formula 2.

In one embodiment of the present specification, the organic light emitting device includes a first electrode; a second electrode; and one or more organic material layers provided between the first electrode and the second electrode, wherein one or more layers of the organic material layers include a cured material of a coating composition including the ionic compound including the anion group of Chemical Formula 1; and the cation group of Chemical Formula 2.

In one embodiment of the present specification, the cured material of the coating composition is in a cured state by heat treating or light treating the coating composition.

In one embodiment of the present specification, the organic material layer including the cured material of the coating composition is a hole injection layer.

In one embodiment of the present specification, the organic material layer including the cured material of the coating composition is a hole injection layer, and the ionic compound including the anion group of Chemical Formula 1; and the cation group of Chemical Formula 2 is included as a dopant of the hole injection layer.

In one embodiment of the present specification, the organic material layer including the cured material of the coating composition is a hole injection layer, and the ionic compound including the anion group of Chemical Formula 1; and the cation group of Chemical Formula 2 is included as a p-doping material of the hole injection layer.

In the present specification, the p-doping material means a material enabling a host material to have a p semiconductor property. The p semiconductor property means a property receiving holes through injection or transferring holes at a highest occupied molecular orbital (HOMO) energy level, that is, a property of a material having high hole conductivity.

In one embodiment of the present specification, the organic material layer formed using the coating composition is a hole injection layer, and the ionic compound including the anion group of Chemical Formula 1; and the cation group of Chemical Formula 2 is a dopant of the hole injection layer, and an arylamine compound is included as a host of the hole injection layer.

In one embodiment of the present specification, the dopant compound and the host compound are included in a weight ratio of 20:1 to 1:1.

In one embodiment of the present specification, the arylamine compound is a monomer or a polymer.

In one embodiment of the present specification, an arylamine compound that is a monomer or a polymer is further included as a host of the hole injection layer.

In one embodiment of the present specification, the arylamine compound includes one of the following-structured curing groups.

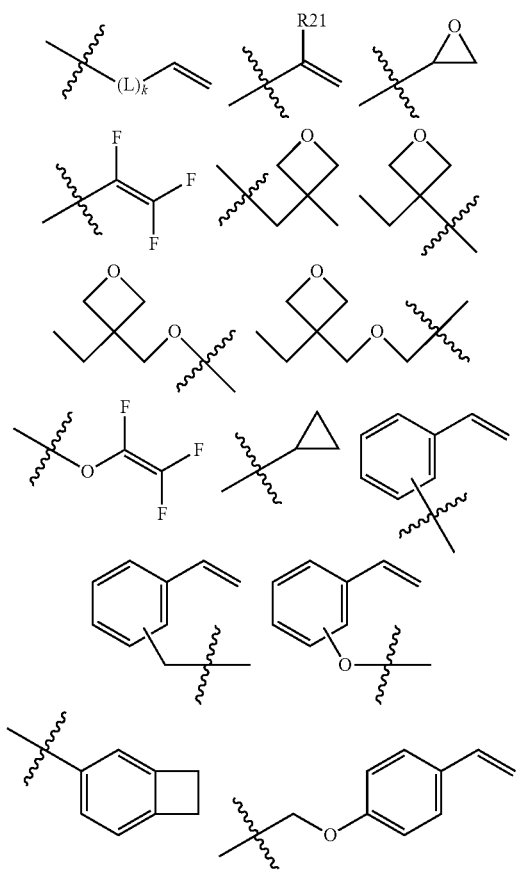

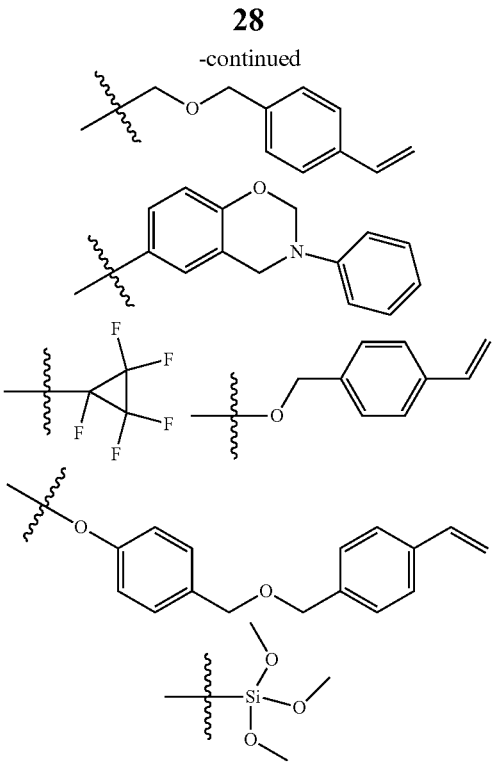

In the structural formulae, L is a direct bond; O; S; a substituted or unsubstituted alkylene group; a substituted or unsubstituted arylene group; or a substituted or unsubstituted divalent heterocyclic group, and k is an integer of 1 or 2, and when k is 2, substituents in the parentheses are different from each other, and R21 is a substituted or unsubstituted alkyl group.

In one embodiment of the present specification, the host of the hole injection layer has a HOMO level from 4.8 eV to 5.8 eV.

The HOMO level of the present specification is measured using an electrochemical cyclic voltammetry method (CV). Onset potential ($E_{onset}$) at which host material oxidation begins is measured, and ferrocene potential ($E_{1/2(Fc)}$) is measured under the same condition. The ferrocene potential is defined as 4.8 eV with respect to a vacuum energy level, and the HOMO level is calculated using the following equation.

$$HOMO(eV)=4.8+(E_{onset}-E_{1/2(Fc)})$$

The arylamine compound forms crosslinking, and an organic material layer including a thin-filmed structure is capable of being provided. In this case, being dissolved by a solvent deposited on a surface of the organic material layer formed using the coating composition, or being morphologically influenced or decomposed may be prevented.

Accordingly, when the organic material layer including the cured material of the coating composition is formed including a step of heat treatment or light treatment, resistance for a solvent increases, and a multilayer may be formed by repeatedly performing solution deposition and crosslinking method, and as a result, a lifetime property of a device may be enhanced due to increased stability.

In one embodiment of the present specification, the organic material layer including the cured material of the coating composition is a hole transfer layer, a hole injection layer, or a layer carrying out hole transfer and hole injection at the same time.

In another embodiment, the organic material layer formed using the coating composition is a light emitting layer.

In one embodiment of the present specification, the organic light emitting device further includes one, two or more layers selected from the group consisting of a hole injection layer, a hole transfer layer. an electron transfer layer, an electron injection layer, an electron blocking layer and a hole blocking layer.

In one embodiment of the present specification, the first electrode is a cathode, and the second electrode is an anode.

In one embodiment of the present specification, the first electrode is an anode, and the second electrode is a cathode.

In another embodiment, the organic light emitting device may be an organic light emitting device having a structure in which an anode, one or more organic material layers and a cathode are consecutively laminated on a substrate (normal type).

In another embodiment, the organic light emitting device may be an organic light emitting device having a structure in a reverse direction in which a cathode, one or more organic material layers and an anode are consecutively laminated on a substrate (inverted type).

The organic material layer of the organic light emitting device of the present specification may be formed in a single layer structure, but may also be formed in a multilayer structure in which two or more organic material layers are laminated. For example, the organic light emitting device of the present disclosure may have a structure including a hole injection layer, a hole transfer layer, a light emitting layer, an electron transfer layer, an electron injection layer and the like as the organic material layer. However, the structure of the organic light emitting device is not limited thereto, and may include less numbers of organic material layers.

For example, a structure of the organic light emitting device according to one embodiment of the present specification is illustrated in FIG. 1.

FIG. 1 illustrates a structure of the organic light emitting device in which an anode (201), a hole injection layer (301), a hole transfer layer (401), a light emitting layer (501), an electron transfer layer (601) and a cathode (701) are consecutively laminated on a substrate (101).

In FIG. 1, the hole injection layer (301), the hole transfer layer (401) and the light emitting layer (501) are formed using a coating composition including the compound represented by Chemical Formula 1.

FIG. 1 illustrates the organic light emitting device, however, the organic light emitting device is not limited thereto.

When the organic light emitting device includes a plurality of organic material layers, the organic material layers may be formed with materials that are the same as or different from each other.

The organic light emitting device of the present specification may be manufactured using materials and methods known in the art, except that one or more layers of the organic material layers are formed using the coating composition including the compound.

For example, the organic light emitting device of the present specification may be manufactured by consecutively laminating an anode, an organic material layer and a cathode on a substrate. Herein, the organic light emitting device may be manufactured by forming an anode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer thereon, and then depositing a material capable of being used as a cathode thereon. In addition to such a method, the organic light emitting device may also be manufactured by consecutively depositing a cathode material, an organic material layer and an anode material on a substrate.

One embodiment of the present specification also provides a method for manufacturing an organic light emitting device formed using the coating composition.

Specifically, the method for manufacturing an organic light emitting device in one embodiment of the present specification includes preparing a substrate; forming a cathode or an anode on the substrate; forming one or more organic material layers on the cathode or the anode; and forming an anode or a cathode on the organic material layers, wherein one or more layers of the organic material layers are formed using the coating composition.

In one embodiment of the present specification, the organic material layer formed using the coating composition is formed using spin coating.

In another embodiment, the organic material layer formed using the coating composition is formed using a printing method.

In an embodiment of the present specification, examples of the printing method include inkjet printing, nozzle printing, offset printing, transfer printing, screen printing or the like, but are not limited thereto.

The coating composition according to one embodiment of the present specification is suited for a solution process due to its structural properties and may be formed using a printing method, and therefore, is economically effective in terms of time and costs when manufacturing a device.

In one embodiment of the present specification, the forming of an organic material layer formed using the coating composition includes coating the coating composition on the cathode or the anode; and heat treating or light treating the coated coating composition.

In one embodiment of the present specification, the time of heat treating the organic material layer formed using the coating composition is preferably within 1 hour and more preferably within 30 minutes.

In one embodiment of the present specification, the atmosphere of heat treating the organic material layer formed using the coating composition is preferably inert gas such as argon or nitrogen.

In addition, the composition according to one embodiment of the present specification may be thin-filmed through heat treatment or light treatment, and may be included as a copolymer using a coating composition mixed with other monomers. In addition, a copolymer or a mixture may be included using a coating composition mixed with other polymers.

As the anode material, materials having large work function are normally preferred so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or LiO$_2$/Al, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suitable. Specific examples thereof include arylamine-based organic materials, conductive polymers, block copolymers having conjugated parts and non-conjugated parts together, and the like, but are not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes (Alq$_3$); carbazole-based compounds; dimerized styryl compounds; BAlq; 10-hydroxybenzo quinoline-metal compounds; benzoxazole-, benzthiazole- and benzimidazole-based compounds; poly(p-phenylenevinylene) (PPV)-based polymers; spiro compounds; polyfluorene, rubrene, and the like, but are not limited thereto.

The light emitting layer may include a host material and a dopant material. The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes carbazole derivatives, dibenzofuran derivatives, ladder-type furan compounds, pyrimidine derivatives and the like, however, the material is not limited thereto.

The dopant material includes aromatic amine derivatives, styrylamine compounds, boron complexes, fluoranthene compounds, metal complexes and the like. Specifically, the aromatic amine derivative is a fused aromatic ring derivative having a substituted or unsubstituted arylamino group and includes arylamino group-including pyrene, anthracene, chrysene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group are substituted or unsubstituted. Specifically, styrylamine, styryldiamine, styryltriamine, styryltetramine or the like is included, however, the styrylamine compound is not limited thereto. In addition, the metal complex includes iridium complexes, platinum complexes or the like, but is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suitable. Specific examples thereof include Al complexes of 8-hydroxyquinoline; complexes including Alq$_3$; organic radical compounds; hydroxyflavon-metal complexes, and the like, but are not limited thereto. The electron transfer layer may be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited there.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)berylium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium and the like, but is not limited thereto.

The hole blocking layer is a layer blocking holes from reaching a cathode, and generally, may be formed under the same condition as the hole injection layer. Specifically, oxadiazole derivatives or triazole derivatives, phenanthroline derivatives, BCP, aluminum complexes and the like are included, however, the material is not limited thereto.

The organic light emitting device according to the present specification may be a top-emission type, a bottom-emission type or a dual-emission type depending on the materials used.

In one embodiment of the present specification, the coating composition may be included in organic solar cells or organic transistors in addition to organic light emitting devices.

Hereinafter, the present specification will be described in detail with reference to examples in order to specifically describe the present specification. However, the examples according to the present specification may be modified to various different forms, and the scope of the present specification is not to be construed as being limited to the examples described below. Examples of the present specification are provided in order to more fully describe the present specification to those having average knowledge in the art.

EXAMPLE

Preparation Example 1

1) Synthesis of Anion Group of Compound 1

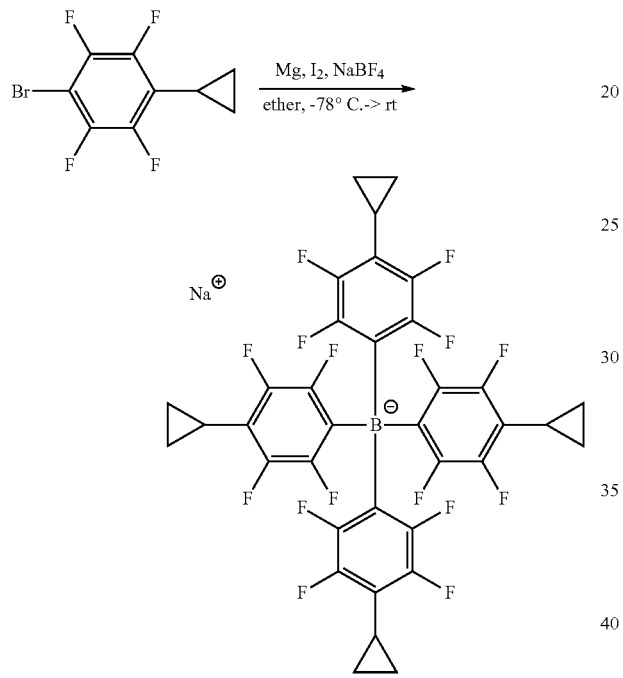

Magnesium (2.3 g, 92.9230 mmol), 1-cyclopropyl-2,3,5,6-tetrafluorostyrene (25 g, 92.9230 mmol), $I_2$ (708 mg, 2.7877 mmol) and ether (310 mL) were introduced to a 1000 mL round bottom flask, and stirred for 3 hours. To the reaction solution, $NaBF_4$ (2.4 g, 22.3015 mmol) was added, and the result was stirred overnight. An aqueous $Na_2CO_3$ solution was added to the reaction solution to terminate the reaction, and the result was extracted using ether. The solvent was removed, and a target compound was used in the next reaction without further purification.

2) Synthesis of Cation Group of Compound 1

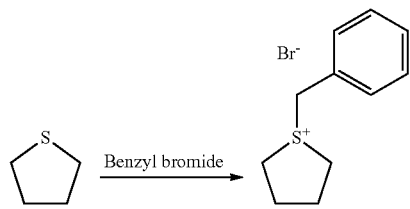 [SMILES: C1CCSC1 ; c1ccc(C[S+]2CCCC2)cc1 ; [Br-]]

Tetrahydrothiophene (25 mL, 292.346 mmol) and benzyl bromide (5000 mg, 29.2346 mmol) were introduced to a 50 mL round bottom flask, and vigorously stirred for 24 hours. The solids were washed using hexane (100 mL) to obtain 8.2 g of a target compound. (Yield: 94%)

3) Synthesis of Compound 1

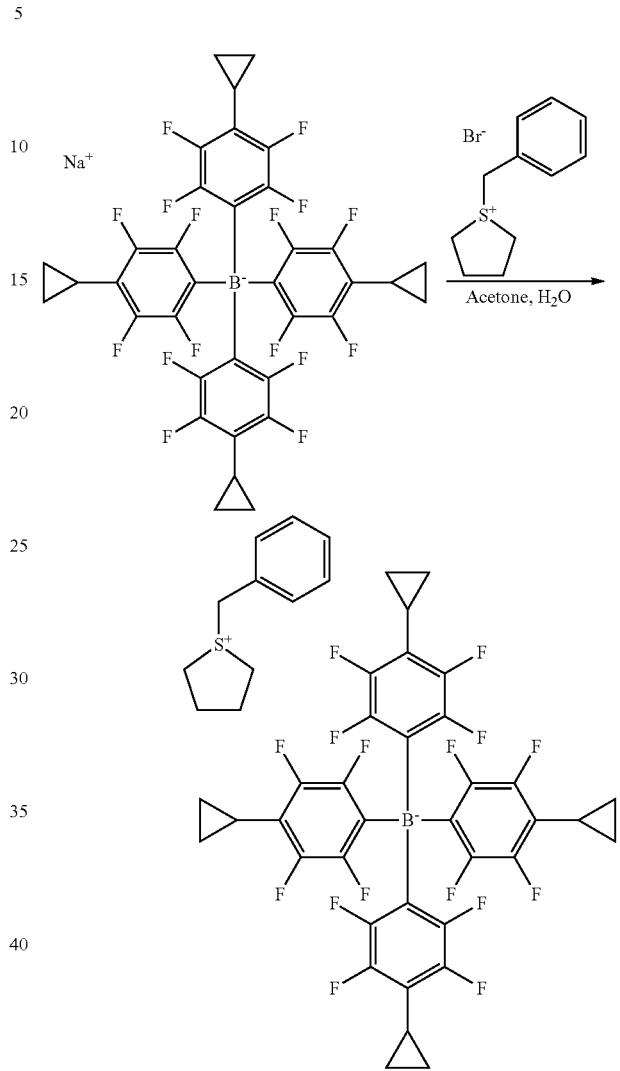

Sodium tetrakis(4-cyclopropyl-2,3,5,6-tetrafluorophenyl)borate (1 g, 1.2653 mmol), 1-benzyltetrahydro-1H-thiophen-1-ium bromide (328 mg, 1.2653 mmol), $H_2O$ (10 mL) and acetone (10 mL) were introduced to a 50 mL round bottom flask, and vigorously stirred for 30 minutes. The result was extracted using dichloromethane (10 mL×3) to remove the solvent, and dried to obtain 1.2 g of a target compound. (Yield: 100%)

Preparation Example 2

1) Synthesis of Anion Group of Compound 2

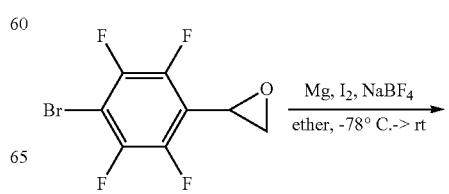

-continued

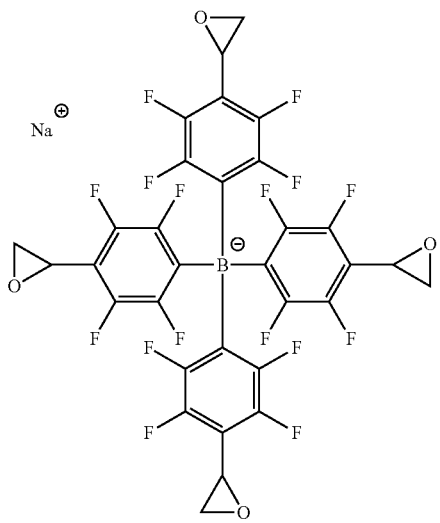

Magnesium (2.2 g, 92.2475 mmol), 1-epoxy-2,3,5,6-tetrafluorostyrene (25 g, 92.2475 mmol), I$_2$ (702 mg, 2.7674 mmol) and ether (310 mL) were introduced to a 1000 mL round bottom flask, and stirred for 3 hours. To the reaction solution, NaBF$_4$ (2.4 g, 22.1394 mmol) was added, and the result was stirred overnight. An aqueous Na$_2$CO$_3$ solution was added to the reaction solution to terminate the reaction, and the result was extracted using ether. The solvent was removed, and a target compound was used in the next reaction without further purification.

2) Synthesis of Cation Group of Compound 2

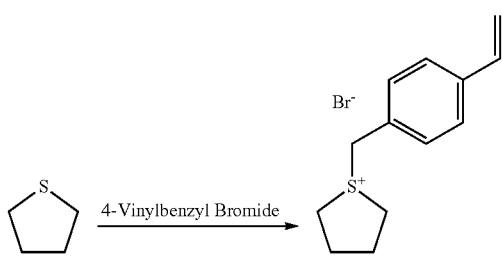

Tetrahydrothiophene (25 mL, 292.346 mmol) and benzyl bromide (5.7 g, 29.2346 mmol) were introduced to a 50 mL round bottom flask, and vigorously stirred for 24 hours. The solids were washed using hexane (100 mL) to obtain 8.1 g of a target compound. (Yield: 98%)

3) Synthesis of Compound 2

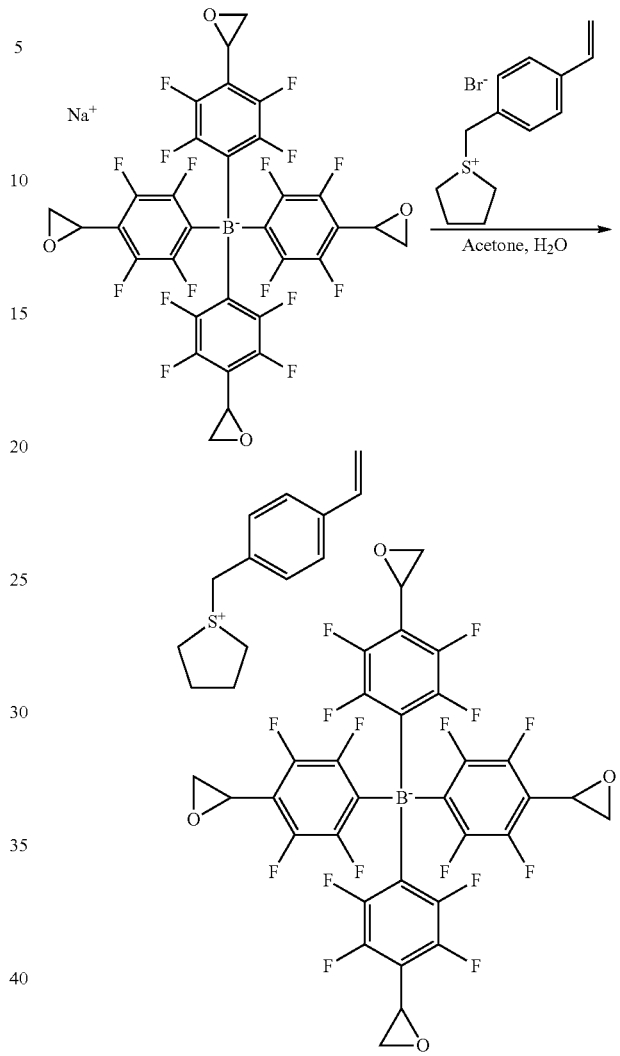

Sodium tetrakis(2,3,5,6-tetrafluoro-4-(oxiran-2-yl)phenyl)borate (2 g, 2.5056 mmol), 1-(4-vinylbenzyl)tetrahydro-1H-thiophen-1-ium bromide (715 mg, 2.5056 mmol), H$_2$O (20 mL) and acetone (20 mL) were introduced to a 50 mL round bottom flask, and vigorously stirred for 30 minutes. The result was extracted using dichloromethane (20 mL×3) to remove the solvent, and dried to obtain 2.5 g of a target compound. (Yield: 100%)

Preparation Example 3

1) Synthesis of Anion Group of Compound 3

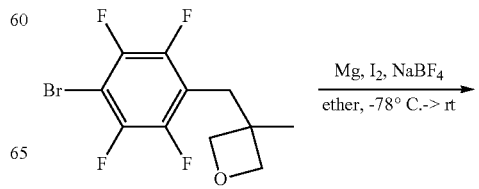

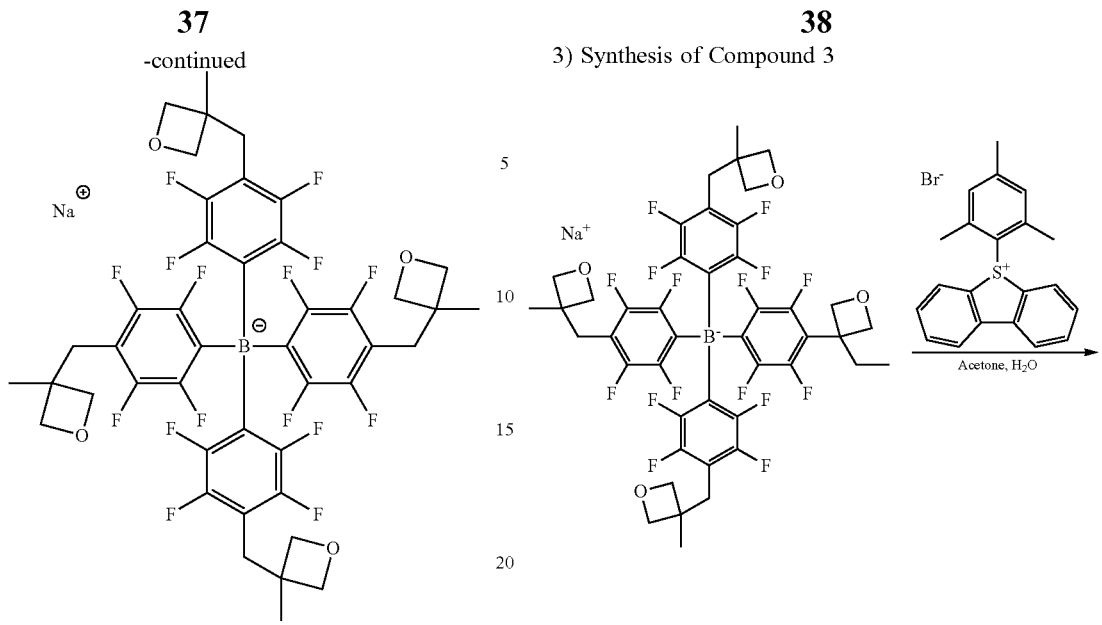

Magnesium (1.9 g, 79.8492 mmol), 3-(4-bromo-2,3,5,6-tetrafluorobenzyl)-3-methyloxetane (25 g, 79.8492 mmol), $I_2$ (608 mg, 2.3955 mmol) and ether (260 mL) were introduced to a 1000 mL round bottom flask, and stirred for 3 hours. To the reaction solution, $NaBF_4$ (2.1 g, 19.1638 mmol) was added, and the result was stirred overnight. An aqueous $Na_2CO_3$ solution was added to the reaction solution to terminate the reaction, and the result was extracted using ether. The solvent was removed, and a target compound was used in the next reaction without further purification.

2) Synthesis of Cation Group of Compound 3

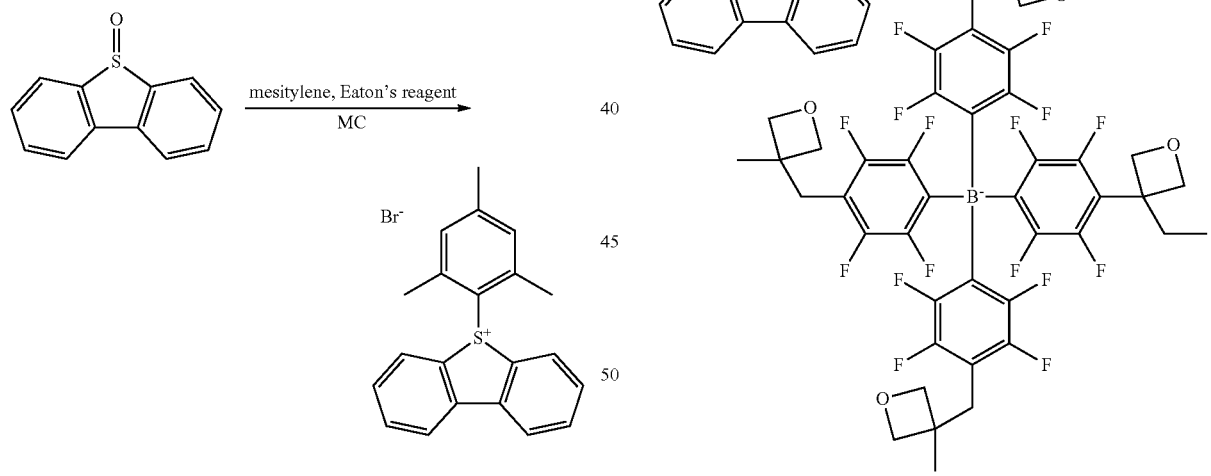

Dibenzothiophene oxide (15.0 g, 74.9 mmol), mesitylene (74.9 mmol) and dichloromethane (200 mL) were introduced to a 250 mL round bottom flask, and Eaton's Reagent (100 mL) was slowly added thereto under a 0° C. condition. The reaction solution was slowly warmed to room temperature, and stirred for 4 hours. At 0° C., water (200 mL) was added thereto to terminate the reaction, and the organic layer was extracted using ethyl acetate (3×100 mL). An aqueous solution dissolving potassium bromide (17.9 g, 0.150 mmol) in water (50 mL) was added to the organic layer, and the result was vigorously stirred for 1 hour. The reaction solution was filtered, then washed using water (3×200 mL) and MTBE (3×200 mL), and dried to obtain 12 g of a target compound. (Yield: 41%)

3) Synthesis of Compound 3

Sodium(4-(3-ethyloxete-3-yl)-2,3,5,6-tetrafluorophenyl) tris(2,3,5,6-tetrafluoro-4-((3-methyloxetan-3-yl)methyl) phenyl)borate (2 g, 2.0692 mmol), 5-mesityl-5H-dibenzo[b,d]thiophen-5-ium bromide (793 mg, 2.0692 mmol), $H_2O$ (20 mL) and acetone (20 mL) were introduced to a 50 mL round bottom flask, and vigorously stirred for 30 minutes. The result was extracted using dichloromethane (20 mL×3) to remove the solvent, and dried to obtain 2.6 g of a target compound. (Yield: 100%)

Preparation Example 4

1) Synthesis of Anion Group of Compound 4

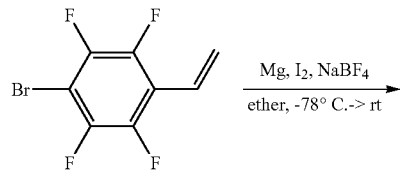

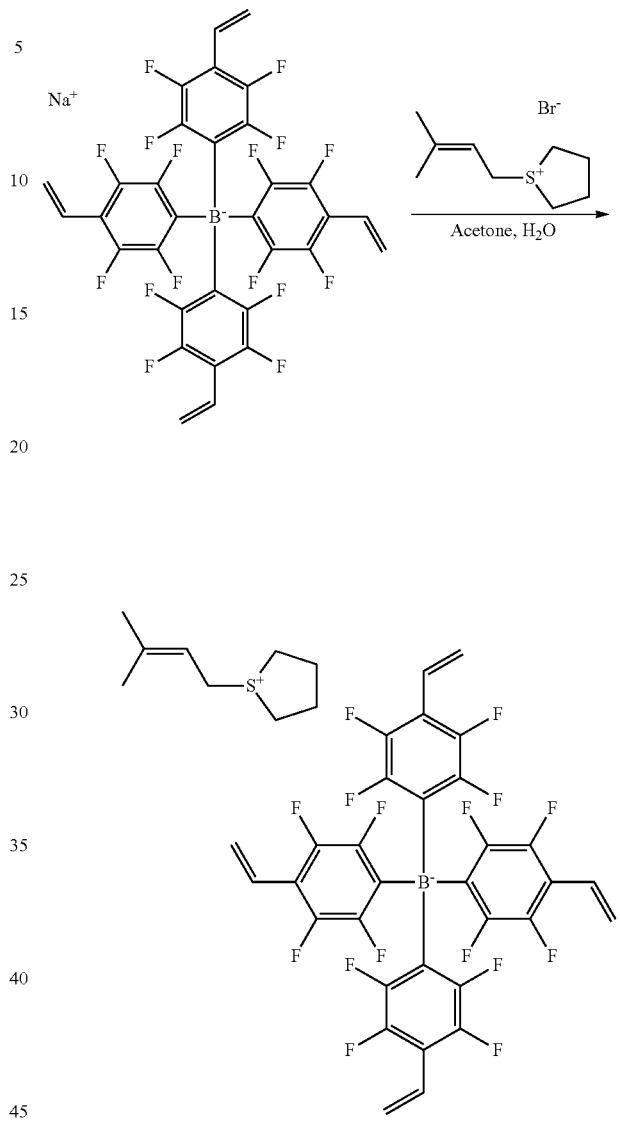

Magnesium (24 g, 98.0354 mmol), 2,3,5,6-tetrafluoro-1-bromostyrene (25 g, 98.0354 mmol), I₂ (746 mg, 2.9411 mmol) and ether (330 mL) were introduced to a 1000 mL round bottom flask, and stirred for 3 hours. To the reaction solution, NaBF₄ (2.5 g, 23.5285 mmol) was added, and the result was stirred overnight. An aqueous Na₂CO₃ solution was added to the reaction solution to terminate the reaction, and the result was extracted using ether. The solvent was removed, and a target compound was used in the next reaction without further purification.

2) Synthesis of Cation Group of Compound 4

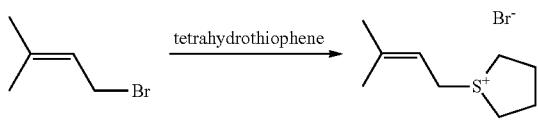

Tetrahydrothiophene (16 mL, 184.5266 mmol) and 1-bromo-3-methylbut-2-ene (5000 mg, 33.5502 mmol) were introduced to a 25 mL round bottom flask, and vigorously stirred for 24 hours. The solids were washed using hexane (100 mL) to obtain 7.4 g of a target compound. (Yield: 93%)

3) Synthesis of Compound 4

Sodium tetrakis(2,3,5,6-tetrafluoro-4-vinylphenyl)borate (2 g, 2.7240 mmol), 1-(3-methylbut-2-en-1-yl)tetrahydro-1H-thiophen-1-ium bromide (646 mg, 2.7240 mmol), H₂O (20 mL) and acetone (20 mL) were introduced to a 50 mL round bottom flask, and vigorously stirred for 30 minutes. The result was extracted using dichloromethane (20 mL×3) to remove the solvent, and dried to obtain 2.3 g of a target compound. (Yield: 100%)

An MS spectrum and a DSC spectrum of Compound 4 are shown in FIG. 2 and FIG. 3.

The DSC data are differential scanning calorimeter data, and curing of the compound was seen through FIG. 3.

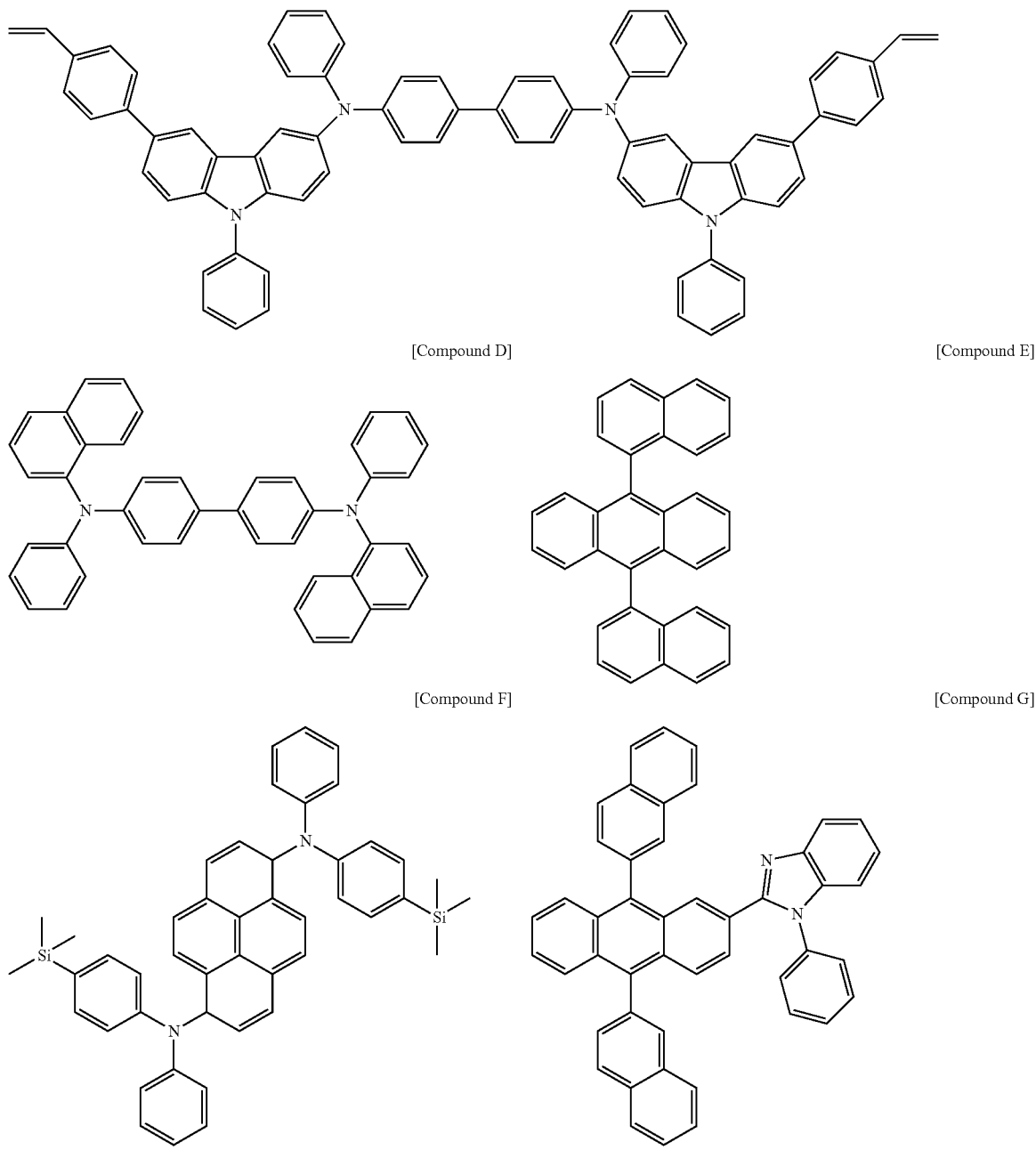

A glass substrate on which indium tin oxide (ITO) was deposited as a thin film to a thickness of 1,500 Å was placed in detergent-dissolved distilled water and ultrasonic cleaned. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol and acetone for 30 minutes each, dried, and then transferred to a glove box.

On the transparent ITO electrode prepared as above, a coating composition was produced by mixing a p doping material represented by Compound 1 of the present disclosure, [Compound A] that is a host compound, and an organic solvent (cyclohexanone), specifically, by mixing Compound 1, Compound A and the organic solvent in a weight ratio of 2:8:490, the coating composition was spin coated to form a hole injection layer having a thickness of 300 Å, and the coating composition was cured for 30 minutes on a hot plate under $N_2$ atmosphere. After that, the result was transferred to a vacuum depositor, and then Compound D was vacuum deposited on the hole injection layer to form a hole transfer layer.

Subsequently, a light emitting layer was formed on the hole transfer layer by vacuum depositing Compound F in a concentration of 8% with respect to Compound E to a thickness of 300 Å. On the light emitting layer, Compound G was vacuum deposited to a thickness of 200 Å to form an electron injection and transfer layer. A cathode was formed on the electron injection and transfer layer by depositing LiF to a thickness of 12 Å and aluminum to a thickness of 2,000 Å in consecutive order.

In the above-mentioned processes, the deposition rates of the organic materials were maintained at 0.4 Å/sec to 0.7 Å/sec, the deposition rates of the LiF and the aluminum of the cathode were maintained at 0.3 Å/sec and 2 Å/sec, respectively, and the degree of vacuum during the deposition was maintained at $2\times10^{-7}$ to $5\times10^{-8}$ torr.

Example 2

An organic light emitting device was manufactured in the same manner as in Example 1, except that Compound 2 was used instead of Compound 1.

Example 3

An organic light emitting device was manufactured in the same manner as in Example 1, except that Compound 3 was used instead of Compound 1.

Example 4

An organic light emitting device was manufactured in the same manner as in Example 1, except that Compound 4 was used instead of Compound 1.

Comparative Example 1

An organic light emitting device was manufactured in the same manner as in Example 1, except that the following Comparative Compound 1 was used instead of Compound 1.

[Comparative Compound 1]

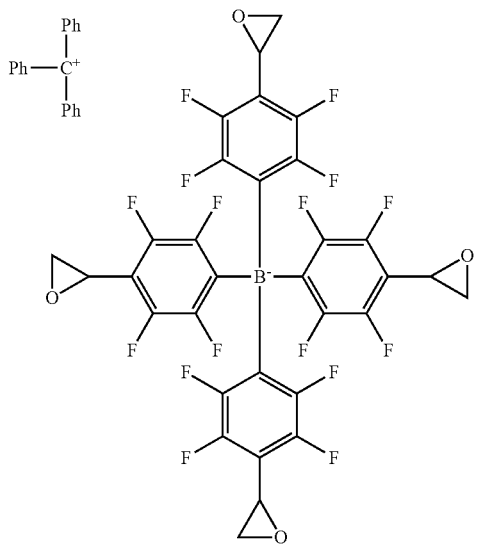

For the organic light emitting devices manufactured in Examples 1 to 4 and Comparative Example 1, a driving voltage, current efficiency, power efficiency and a lifetime were measured, and the results are shown in Table 1.

TABLE 1

| Example | Driving Voltage (V) | Current Efficiency (cd/A) | Power Efficiency (lm/W) | Lifetime (95%, h) |
|---|---|---|---|---|
| Example 1 | 4.24 | 5.68 | 4.21 | 65 |
| Example 2 | 4.30 | 6.63 | 4.84 | 81 |
| Example 3 | 4.74 | 6.96 | 4.61 | 76 |
| Example 4 | 4.22 | 5.55 | 4.13 | 70 |
| Comparative Example 1 | 4.13 | 5.58 | 4.24 | 5 |

The invention claimed is:
1. An ionic compound comprising:
an anion group represented by the following Chemical Formula 1; and
a cation group represented by the following Chemical Formula 2:

[Chemical Formula 1]

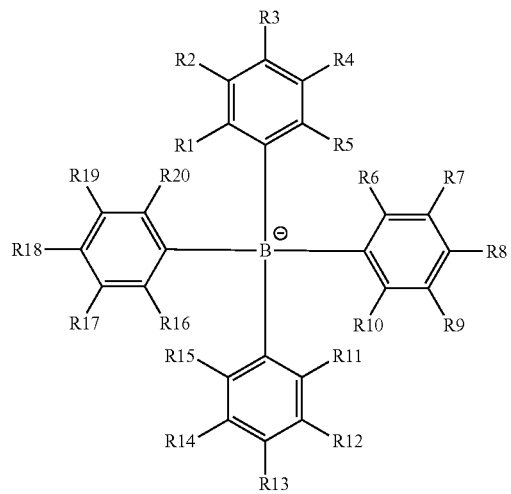

in Chemical Formula 1,
at least one of R1 to R20 is F, a cyano group, or a substituted or unsubstituted fluoroalkyl group;
at least one of the remaining R1 to R20 is a curing group;
the remaining R1 to R20 if present are the same as or different from each other, and each independently hydrogen; deuterium; a nitro group; —C(O)$R_{100}$; —O$R_{101}$; —S$R_{102}$; —SO$_3R_{103}$; —COO$R_{104}$; —OC(O)$R_{105}$; —C(O)N$R_{106}R_{107}$; a substituted or unsubstituted alkyl group; a substituted or unsubstituted fluoroalkyl group; a substituted or unsubstituted alkenyl group; a substituted or unsubstituted alkynyl group; a substituted or unsubstituted amine group; a substituted or unsubstituted aryl group; or a substituted or unsubstituted heterocyclic group; and
$R_{100}$ to $R_{107}$ are the same as or different from each other, and each independently hydrogen; deuterium; or a substituted or unsubstituted alkyl group,

[Chemical Formula 2]

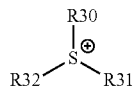

in Chemical Formula 2,

R30 to R32 are the same as or different from each other, and each independently a substituted or unsubstituted alkyl group; a substituted or unsubstituted alkenyl group; a substituted or unsubstituted alkynyl group; a substituted or unsubstituted cycloalkyl group; or a substituted or unsubstituted aryl group; or a substituted or unsubstituted heterocyclic group, and R30 to R32 are each optionally connected to each other to form a ring, wherein the compound represented by Chemical Formula 2 is selected from among the following structural formulae:

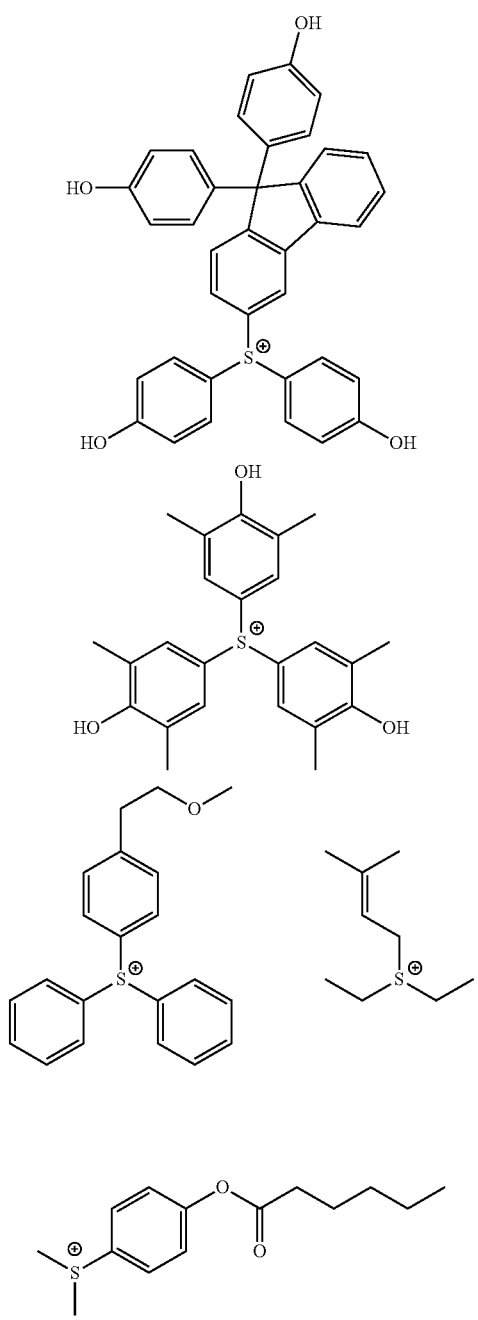

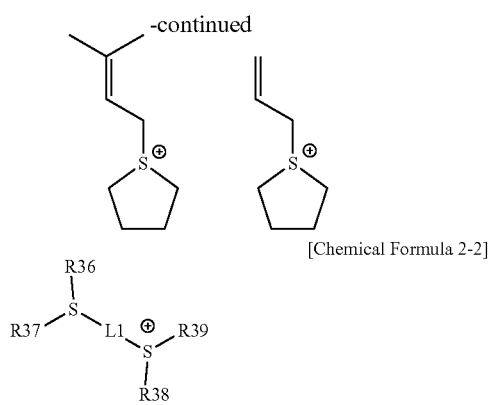

[Chemical Formula 2-2]

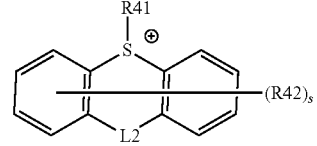

[Chemical Formula 2-4]

in Chemical Formulae 2-2 and 2-4,

R36 to R39 and R41 are the same as or different from each other, and each independently a substituted or unsubstituted alkyl group; a substituted or unsubstituted alkenyl group; a substituted or unsubstituted cycloalkyl group; or a substituted or unsubstituted aryl group;

L1 is a substituted or unsubstituted arylene group;

L2 is a direct bond; O; S; or C=O; and

R42 is a substituted or unsubstituted carbonyl group, and s is 0 or 1.

2. The ionic compound of claim 1, wherein the compound represented by Chemical Formula 2 is selected from among the following structural formulae:

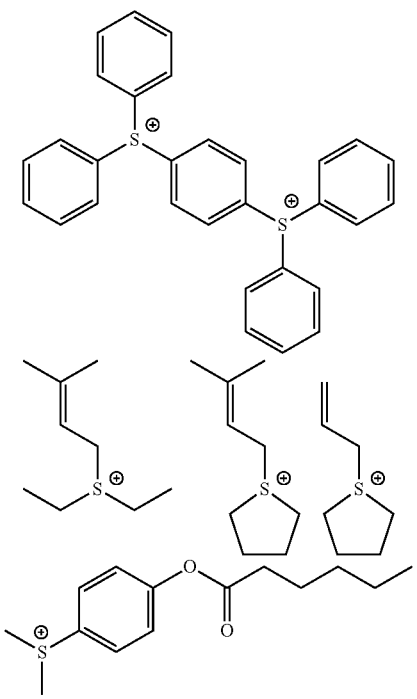

-continued

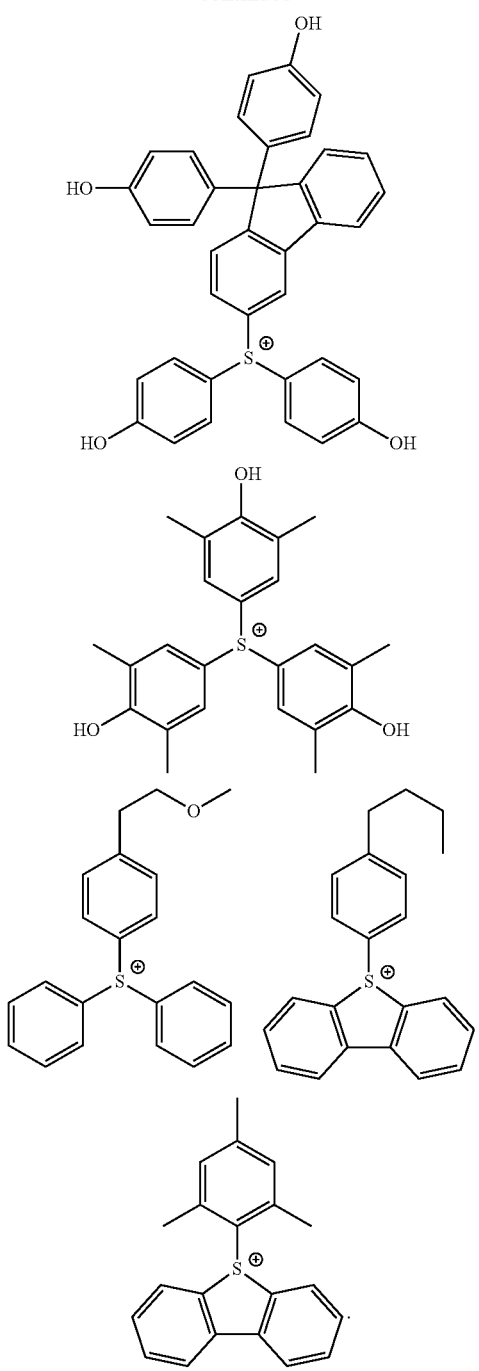

3. The ionic compound of claim 1, wherein the anion group represented by Chemical Formula 1 is represented by the following Chemical Formula 1-1:

[Chemical Formula 1-1]

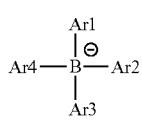

in Chemical Formula 1-1,

Ar1 to Ar4 are the same as or different from each other, at least one of Ar1 to Ar4 is represented by the following Chemical Formula 1-2, and the remaining Ar1 to Ar4 if present are represented by the following Chemical Formula 1-3:

[Chemical Formula 1-2]

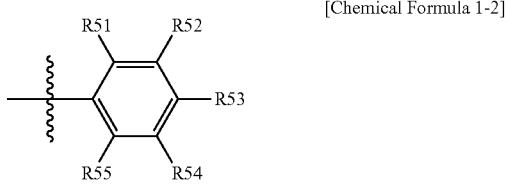

in Chemical Formula 1-2, at least one of R51 to R55 is F, a cyano group, or a substituted or unsubstituted fluoroalkyl group;

at least one of the remaining R51 to R55 is a curing group;

the remaining R51 to R55 if present are the same as or different from each other, and each independently hydrogen; deuterium; a nitro group; —C(O)R$_{100}$; —OR$_{101}$; —SR$_{102}$; —SO$_3$R$_{103}$; —COOR$_{104}$; —OC(O)R$_{105}$; —C(O)NR$_{106}$R$_{107}$; a substituted or unsubstituted alkyl group; a substituted or unsubstituted alkenyl group; a substituted or unsubstituted alkynyl group; a substituted or unsubstituted amine group; a substituted or unsubstituted aryl group; or a substituted or unsubstituted heterocyclic group; and R$_{100}$ to R$_{107}$ are the same as or different from each other, and each independently hydrogen; deuterium; or a substituted or unsubstituted alkyl group,

[Chemical Formula 1-3]

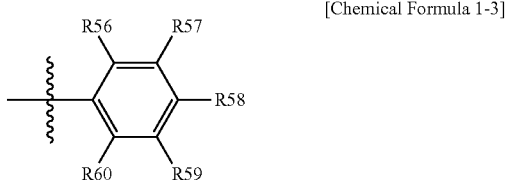

in Chemical Formula 1-3, at least one of R56 to R60 is a curing group; and the remaining R56 to R60 if present are the same as or different from each other, and each independently hydrogen; deuterium; a nitro group; —C(O)R$_{100}$; —OR$_{101}$; —SR$_{102}$; —SO$_3$R$_{103}$; —COOR$_{104}$; —OC(O)R$_{105}$; —C(O)NR$_{106}$R$_{107}$; a substituted or unsubstituted alkyl group; a substituted or unsubstituted fluoroalkyl group; a substituted or unsubstituted alkenyl group; a substituted or unsubstituted alkynyl group; a substituted or unsubstituted amine group; a substituted or unsubstituted aryl group; or a substituted or unsubstituted heterocyclic group, and R$_{100}$ to R$_{107}$ are the same as or different from each other, and each independently hydrogen; deuterium; or a substituted or unsubstituted alkyl group.

4. The ionic compound of claim 1, wherein the curing group is selected from a group of the following curing groups:

[group of curing groups]

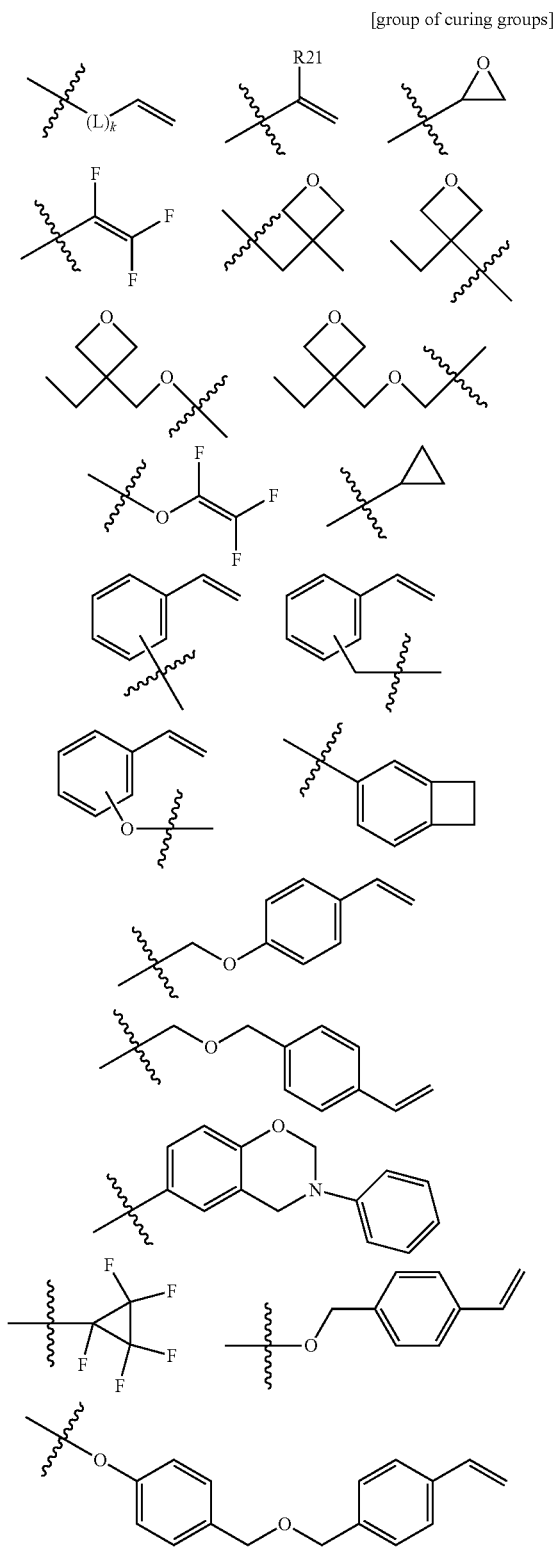

in the group of the curing groups, L is a direct bond; O; S; a substituted or unsubstituted alkylene group; a substituted or unsubstituted arylene group; or a substituted or unsubstituted divalent heterocyclic group;

k is an integer of 1 or 2, and when k is 2, Ls are the same as or different from each other; and R21 is a substituted or unsubstituted alkyl group.

5. The ionic compound of claim 1, wherein the number of the curing group of the anion group represented by Chemical Formula 1 is 4.

6. The ionic compound of claim 1, wherein parts by weight of the F in the anion group is from 10 parts by weight to 45 parts by weight with respect to 100 parts by weight of the anion group.

7. The ionic compound of claim 1, wherein at least one benzene ring among the R1 to R5-bonding benzene ring, the R6 to R10-bonding benzene ring, the R11 to R15-bonding benzene ring, and the R16 to R20-bonding benzene ring in Chemical Formula 1 is selected from among the following structural formulae:

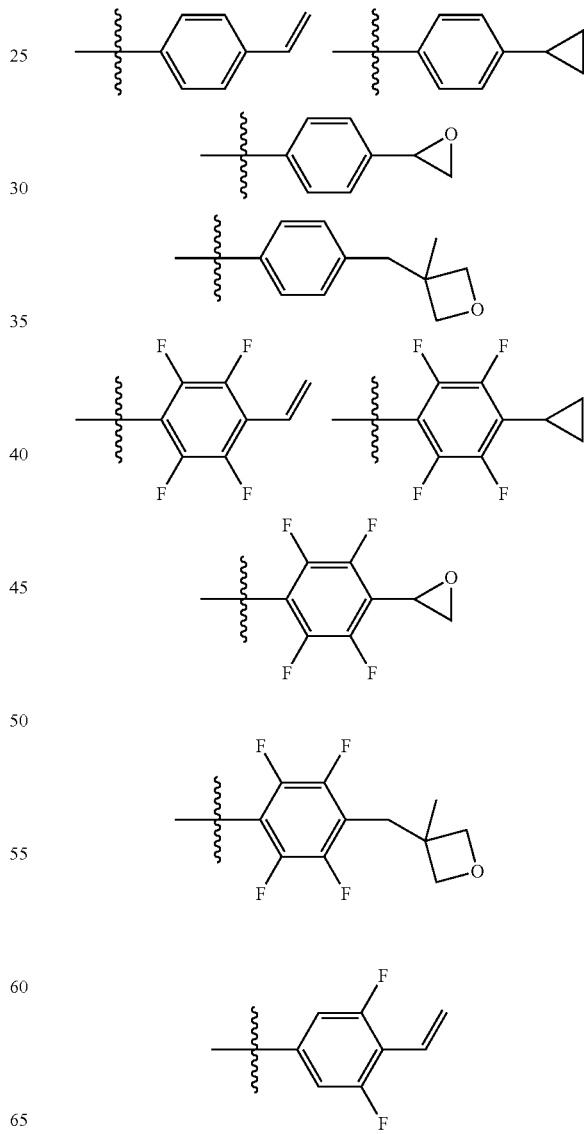

51
-continued
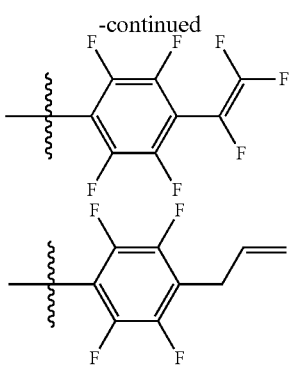
52
-continued
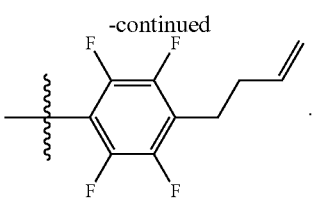
8. The ionic compound of claim 1, wherein the anion group is any one selected from among the following structural formulae:
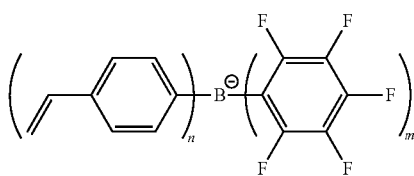 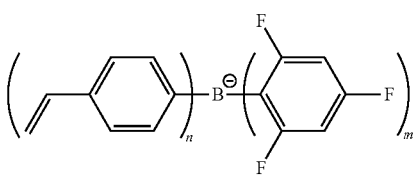
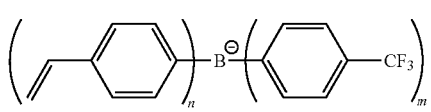 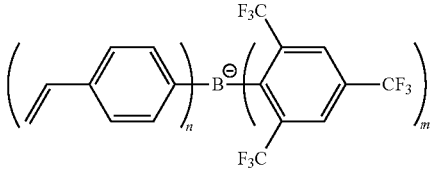
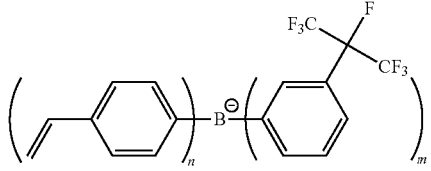 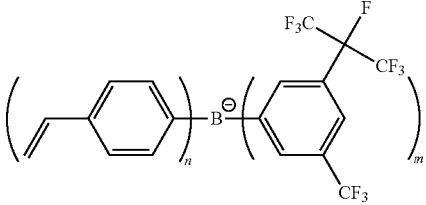
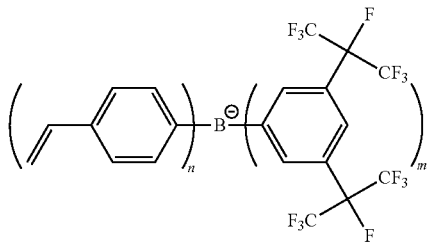 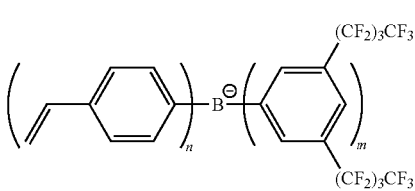
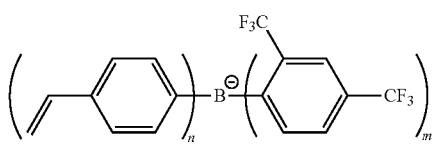 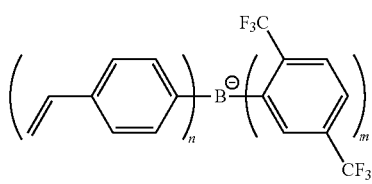
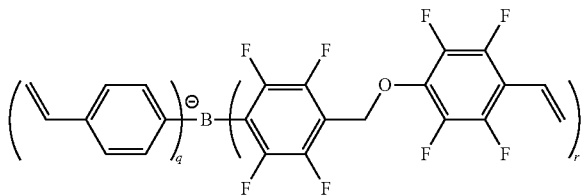 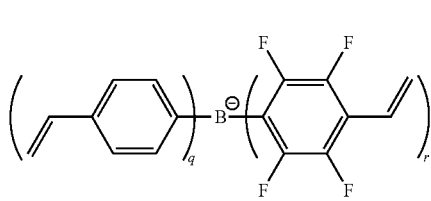

53 54
-continued
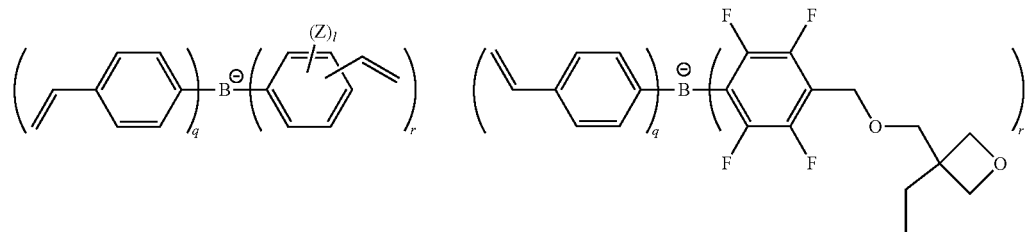
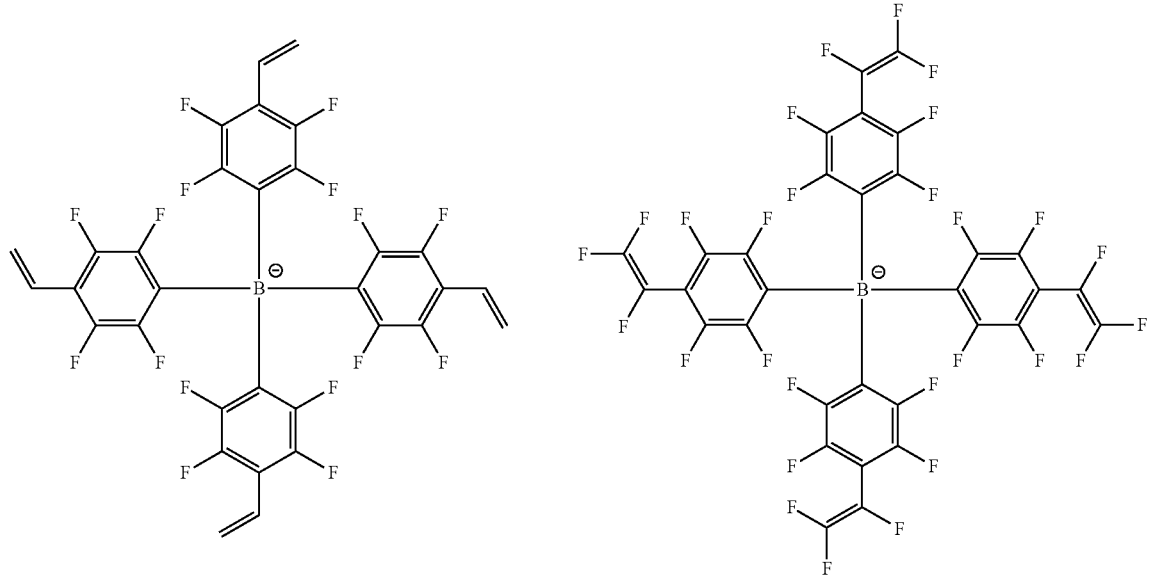
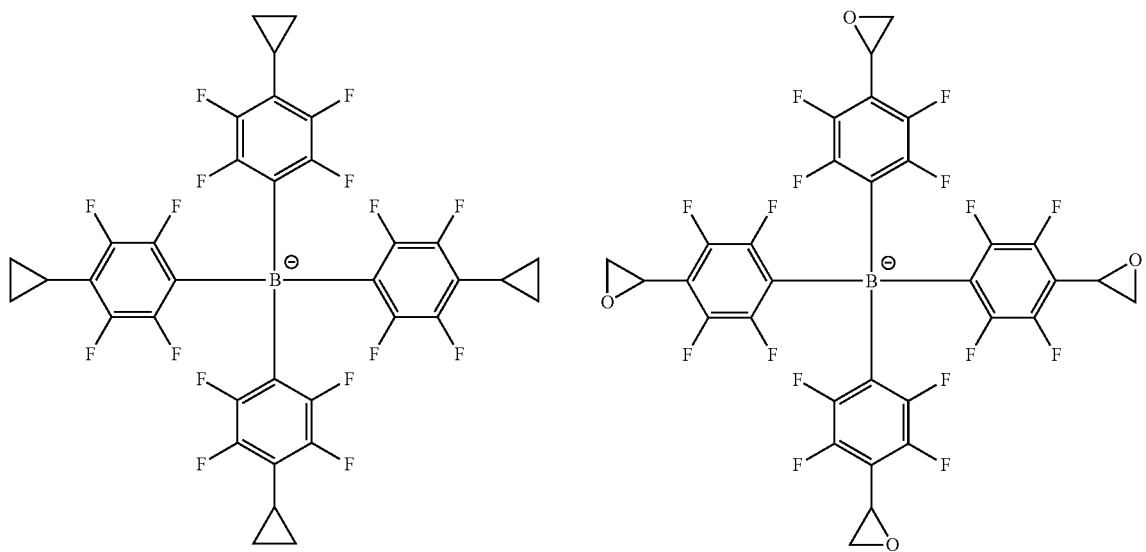

55
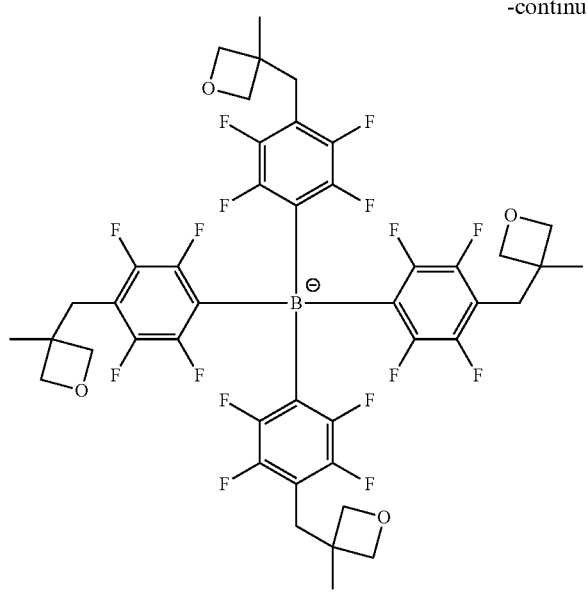
-continued
56
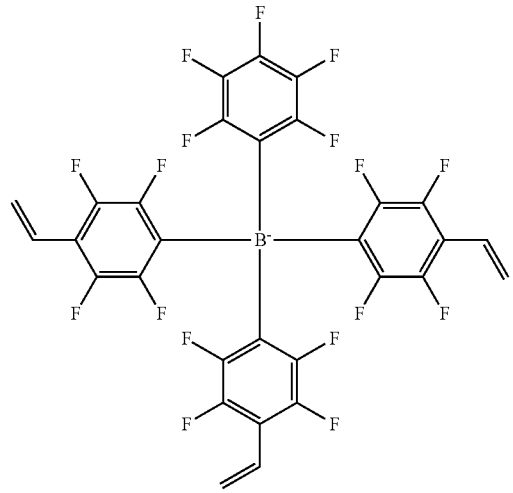
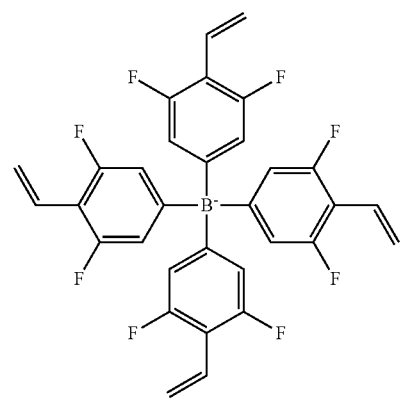

-continued
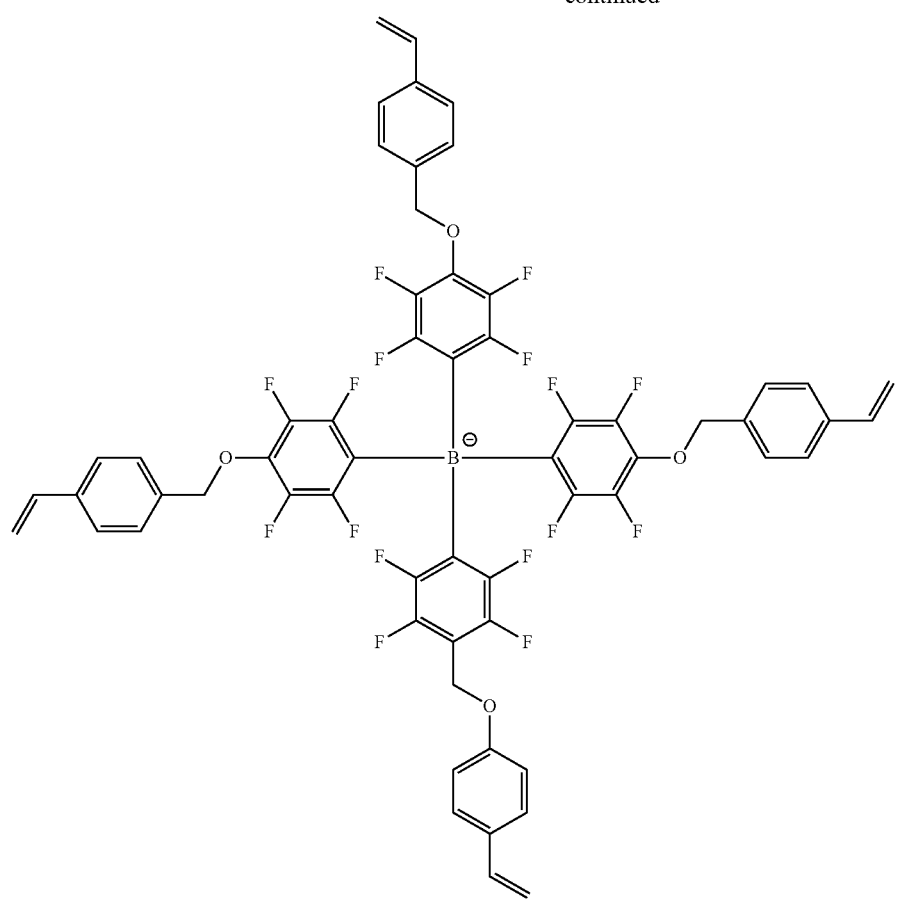
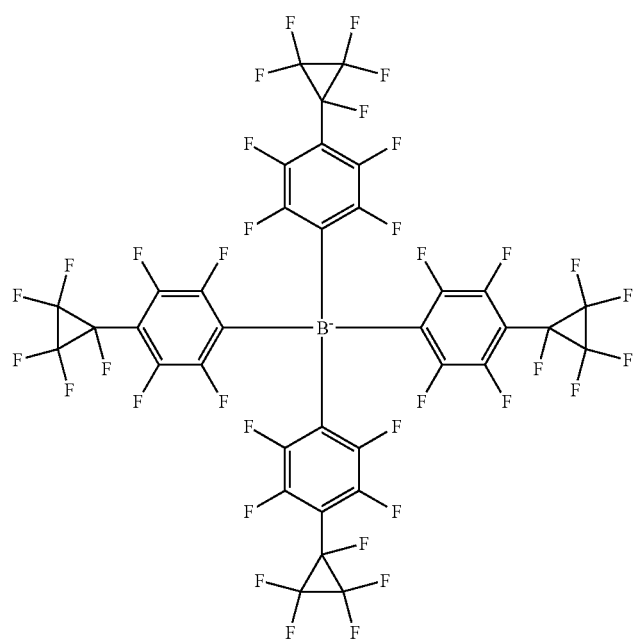

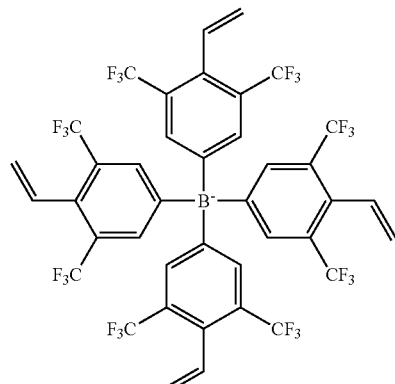
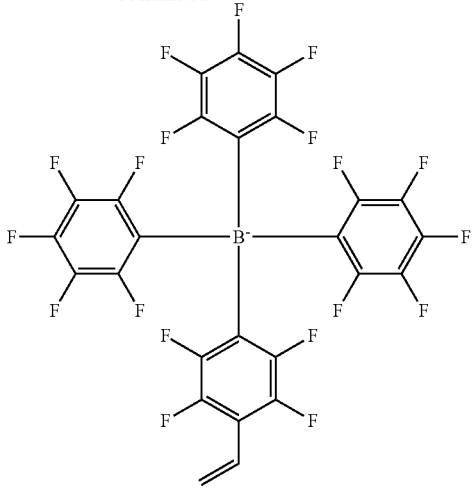

in the structural formulae, n is an integer of 1 to 3, m is an integer of 1 to 3, and m+n=4;

q is an integer of 0 to 3, r is an integer of 1 to 4, and q+r=4;

Z is deuterium; a halogen group; a nitro group; a cyano group; an amino group; —C(O)R$_{100}$; —OR$_{101}$; —SR$_{102}$; —SO$_3$R$_{103}$; —COOR$_{104}$; —OC(O)R$_{105}$; —C(O)NR$_{106}$R$_{107}$; a substituted or unsubstituted alkyl group; a substituted or unsubstituted alkenyl group; a substituted or unsubstituted alkynyl group; a substituted or unsubstituted amine group; a substituted or unsubstituted aryl group; or a substituted or unsubstituted heterocyclic group;

l is an integer of 1 to 4, and when l is 2 or greater, Zs are the same as or different from each other; and R$_{100}$ to R$_{107}$ are the same as or different from each other, and each independently hydrogen; deuterium; or a substituted or unsubstituted alkyl group.

9. The ionic compound of claim 1, which is selected from among the following structural formulae:

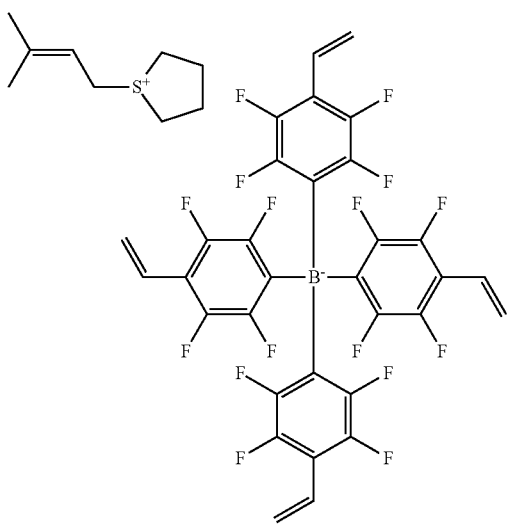

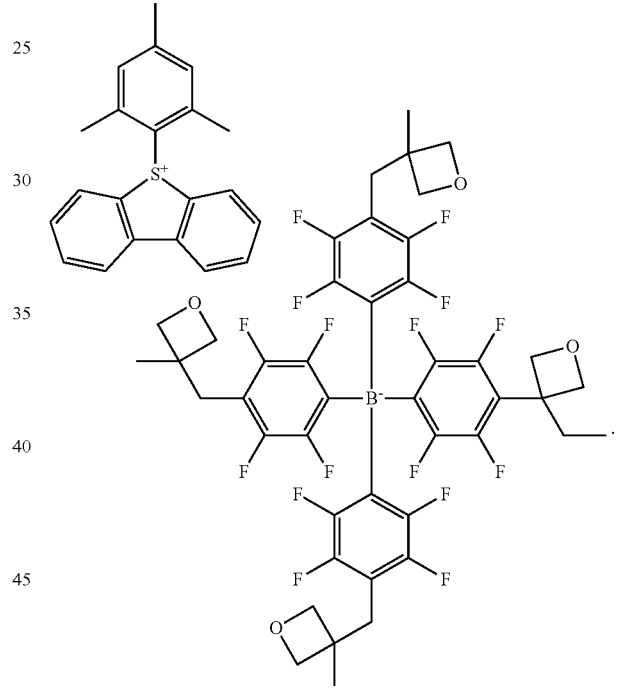

10. A coating composition comprising the ionic compound of claim 1.

11. The coating composition of claim 10, which is for an organic light emitting device.

12. An organic light emitting device comprising:
a first electrode;
a second electrode; and
one or more organic material layers provided between the first electrode and the second electrode,
wherein one or more layers of the organic material layers include a cured material of the coating composition of claim 10.

13. The organic light emitting device of claim 12, wherein the cured material of the coating composition is in a cured state by heat treating or light treating the coating composition.

14. The organic light emitting device of claim 12, wherein the organic material layer including the cured material of the coating composition is a hole injection layer.

15. The organic light emitting device of claim 14, wherein the cured material of the coating composition is included as a p-doping material of the hole injection layer.

16. The organic light emitting device of claim 12, further comprising an arylamine compound that is a monomer or a polymer as a host of the hole injection layer.

17. The organic light emitting device of claim 16, wherein the arylamine compound includes one of the following-structured curing groups:

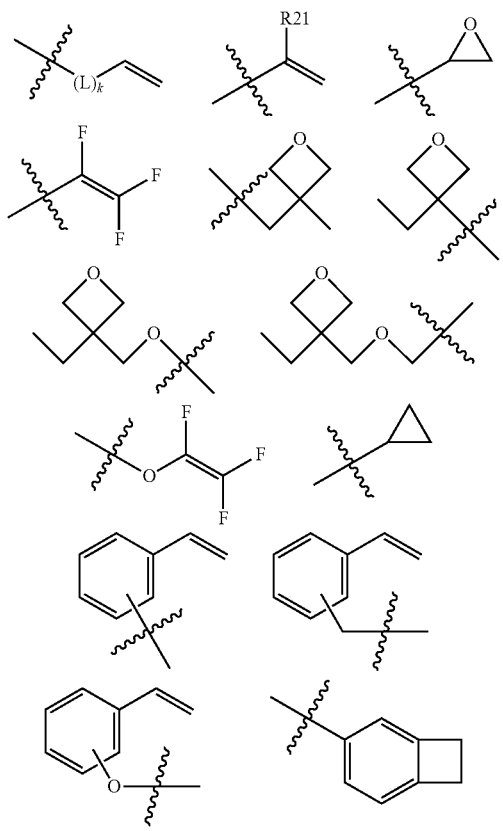

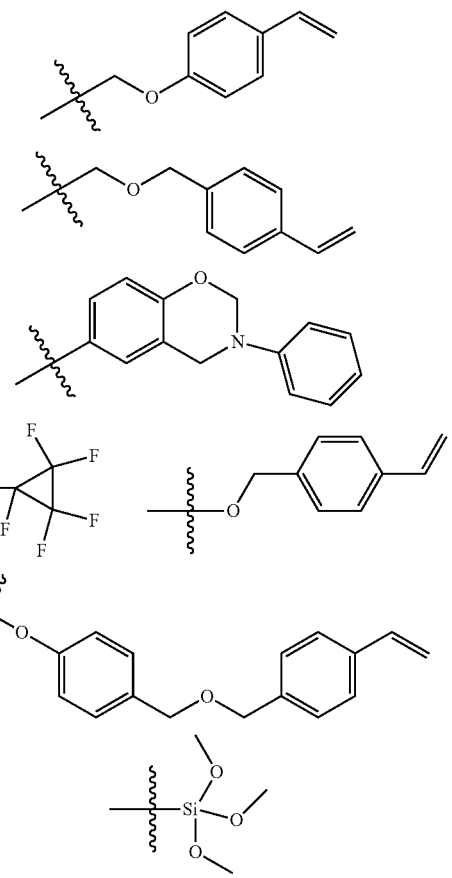

in the structural formulae, L is a direct bond; O; S; a substituted or unsubstituted alkylene group; a substituted or unsubstituted arylene group; or a substituted or unsubstituted divalent heterocyclic group; and k is an integer of 1 or 2, and when k is 2, Ls are different from each other, and R21 is a substituted or unsubstituted alkyl group.

* * * * *